United States Patent
Yin et al.

(10) Patent No.: US 7,804,935 B2
(45) Date of Patent: Sep. 28, 2010

(54) FUZZY LOGIC GUIDED INVERSE TREATMENT PLANNING

(75) Inventors: Fang-Fang Yin, Detroit, MI (US); Jae Ho Kim, Detroit, MI (US); Hui Yan, Detroit, MI (US)

(73) Assignee: Henry Ford Health System, Detroit, MI (US)

( * ) Notice: Subject to any disclaimer, the term of this patent is extended or adjusted under 35 U.S.C. 154(b) by 0 days.

(21) Appl. No.: 10/570,227

(22) PCT Filed: Aug. 27, 2004

(86) PCT No.: PCT/US2004/027893
§ 371 (c)(1),
(2), (4) Date: Sep. 20, 2006

(87) PCT Pub. No.: WO2005/021085
PCT Pub. Date: Mar. 10, 2005

(65) Prior Publication Data
US 2007/0081629 A1    Apr. 12, 2007

Related U.S. Application Data

(60) Provisional application No. 60/498,742, filed on Aug. 28, 2003.

(51) Int. Cl.
*A61N 5/10* (2006.01)

(52) U.S. Cl. ......................................................... 378/65

(58) Field of Classification Search ..................... 378/65
See application file for complete search history.

(56) References Cited

U.S. PATENT DOCUMENTS

| 5,373,844 | A | * | 12/1994 | Smith et al. | .................. | 600/427 |
| 5,995,866 | A | * | 11/1999 | Lemelson | .................... | 600/476 |
| 6,167,294 | A | * | 12/2000 | Busch | ........................ | 600/425 |
| 6,504,899 | B2 | * | 1/2003 | Pugachev et al. | ............. | 378/65 |

OTHER PUBLICATIONS

Bezdek, J.C. et al. "Review of MR image segmentation techniques using pattern recognition" J. of Med. Phys. 20 (4) Jul./Aug. 1993. pp. 1033-1048.*
Rowbottom, Carl Graham et al. "Beam-orientation customization using an artificial neural network" Phys. Med. Biol. 44 (1999) pp. 2251-2262.*
Hosseini-Ashrafi, M E et al. "Pre-optimization of radiotherapy treatment planning: an artificial neural network classification aided technique" Phys. Med. Biol. 44 (1999) pp. 1513-1528.*

* cited by examiner

*Primary Examiner*—Edward J Glick
*Assistant Examiner*—Thomas R Artman
(74) *Attorney, Agent, or Firm*—Kohn & Associates PLLC

(57) ABSTRACT

A fuzzy inference system for use in modulating radiation treatment includes a fuzzifer for inputting imaging data, and inference device operatively to the fuzzifer for analyzing the imaging data and determining radiation treatment target from non-treatment target, and a defuzzifier for modulating radiation treatment pursuant to the analysis from the inference device.

11 Claims, 6 Drawing Sheets

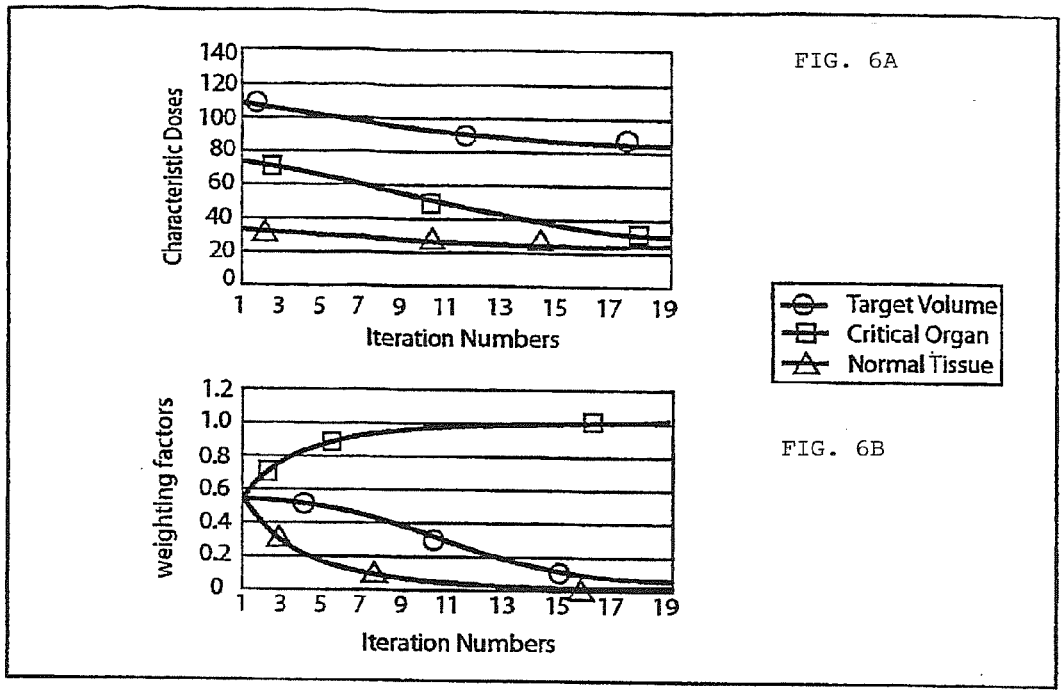
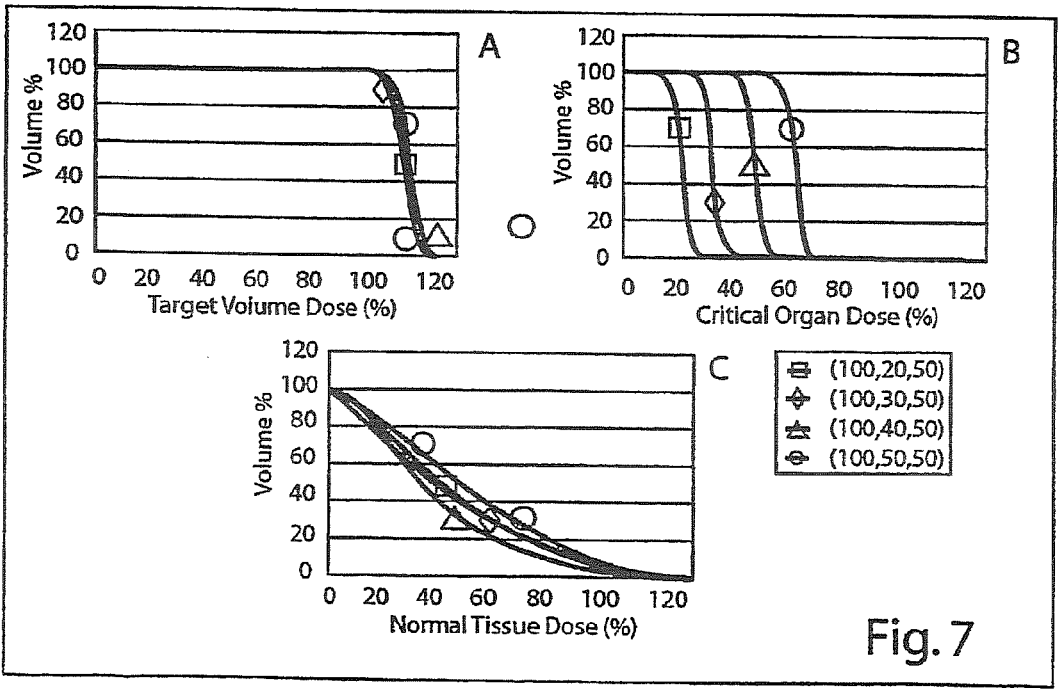

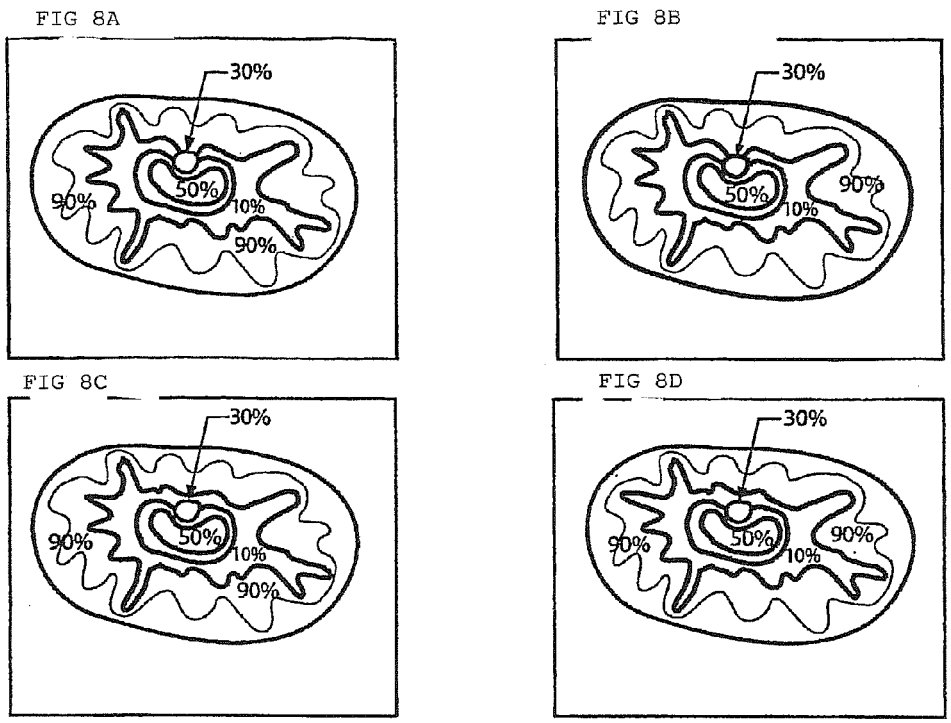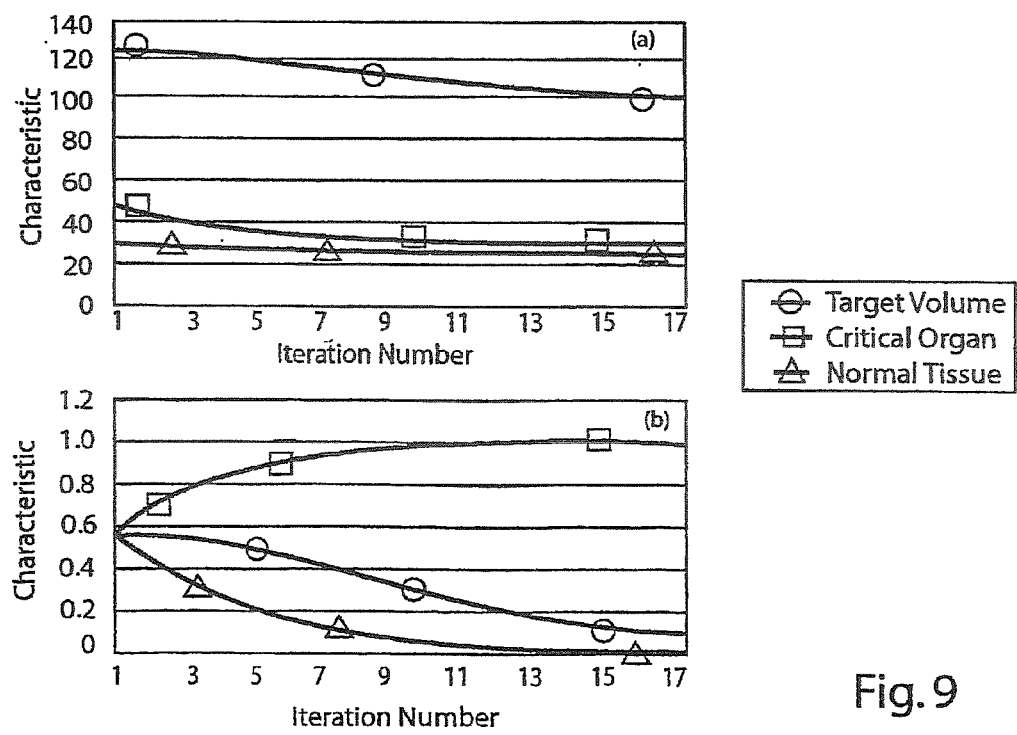
Fig. 9

FUZZY LOGIC GUIDED INVERSE TREATMENT PLANNING

CROSS-REFERENCE TO RELATED APPLICATIONS

This is a National Phase Filing Under 35 U.S.C. 371, of International Application No. PCT/US04/27893, filed Aug. 27, 2004, which claims priority to U.S. Provisional Patent Application Ser. No. 60/498,742, filed Aug. 28, 2003, both of which are incorporated herein by reference.

BACKGROUND OF THE INVENTION

1. Technical Field

Generally, the present invention relates to inverse treatment planning. More specifically, the present invention relates to an artificial intelligence method for guiding inverse treatment planning.

2. Description of the Related Art

Modern day radiation therapy of tumors has two goals: eradication of the tumor and avoidance of damage to healthy tissue and organs present near the tumor. It is known that a vast majority of tumors can be eradicated completely if a sufficient radiation dose is delivered to the tumor; however, complications may result from use of the necessary effective radiation dose. Most complications are due to damage to healthy tissue that surrounds the tumor or to other healthy body organs located close to the tumor. The goal of conformal radiation therapy is to confine the delivered radiation dose to only the tumor volume defined by the outer surfaces of the tumor, while minimizing the dose of radiation applied to surrounding healthy tissue or adjacent healthy organs.

Conformal radiation therapy has been traditionally approached through a range of techniques and typically uses a linear accelerator ("LINAC") as the source of the radiation beam used to treat the tumor. The linear accelerator typically has a radiation beam source that is rotated about the patient and directs the radiation beam toward the tumor to be treated. The beam intensity of the radiation beam has a predetermined, constant beam intensity. Multileaf collimators, which have multiple leaf or finger projections that can be moved individually into and out of the path of the radiation beam, can be programmed to follow the spatial contour of the tumor as seen by the radiation beam as it passes through the tumor, or the "beam's eye view" of the tumor during the rotation of the radiation beam source, which is mounted on a rotatable gantry of the linear accelerator. The multiple leaves of the multileaf collimator form an outline of the tumor shape, as presented by the tumor volume in the direction of the path of travel of the radiation beam, and thus block the transmission of radiation to tissue disposed outside the tumor's spatial outline as presented to the radiation beam, dependent upon the beam's particular radial orientation with respect to the tumor volume.

Another approach to conformal radiation therapy involves the use of independently controlled collimator jaws that can scan a slit field across a stationary patient at the same time that a separate set of collimator jaws follows the target volume as the gantry of the linear accelerator rotates. An additional approach has been the use of attachments for LINACs that allow a slit to be scanned across the patient, the intensity of the radiation beam in the entire slit being modified as the slit is being scanned.

A further approach for conformal radiation therapy treatment has been the use of a narrow pencil beam of high energy photons, with energy that can be varied, and the beam is scanned over the tumor target volume so as to deliver the best possible radiation dose distribution in each orientation of the gantry upon which the photon beam source is mounted.

A major problem associated with such prior art methods of conformal radiation therapy are that if the tumor volume has concave borders, or surfaces, varying the spatial configuration, or contour, of the radiation beam, the therapy is only successful part of the time. In particular, when the convolutions, or outer surfaces, of a tumor are re-entrant, or concave, in a plane parallel to the path of the radiation treatment beam, healthy tissue or organs may be disposed within the concavities formed by the outer tumor concave surfaces, as well as the fact that the thickness of the tumor varies along the path of the radiation beam.

In order to be able to treat tumors having concave borders, it is necessary to vary the intensity of the radiation beam across the surface of the tumor, as well as vary the outer configuration of the beam to conform to the shape of the tumor presented to the radiation beam. The beam intensity of each radiation beam segment should be able to be modulated to have a beam intensity related to the thickness of the portion of the tumor through which the radiation beam passes. For example, where the radiation beam is to pass through a thick section of a tumor, the beam intensity should be higher than when the radiation beam passes through a thin section of the tumor.

Dedicated scanning beam therapy machines have been developed wherein beam intensity modulation can be accomplished through the use of a scanning pencil beam of high-energy photons. The beam intensity of this device is modulated by increasing the power of its electron gun generating the beam. The power increase is directed under computer control as the gun is steered around the tumor by moving the gantry upon which it is mounted and the table upon which the patient lies. The effect is one of progressively "painting" the target with the thickness, or intensity, of the paint, or radiation beam intensity, being varied by the amount of paint on the brush, or how much power is applied to the electron gun, as the electron gun moves over the tumor. Such dedicated scanning beam therapy machines, which utilize direct beam energy modulation, are expensive and quite time consuming in their use and operation, and are believed to have associated with them a significant patient liability due to concerns over the computer control of the treatment beam itself.

Other methods and apparatus for conformal radiation therapy have been developed that spatially modulate the beam intensity of a radiation beam across a volume of tissue in accordance with the thickness of the tumor in the volume of tissue by utilizing a plurality of radiation beam segments. Such methods and apparatus utilize attenuating leaves, or shutters, in a rack positioned within the radiation beam before the beam enters the patient. The tumor is exposed to radiation in slices, each slice being selectively segmented by the shutters. However, a minor disadvantage of that method and apparatus results from the fact that only two slices of tissue volume may be treated with one rotation of the gantry of the linear accelerator. Although the slices may be of arbitrary thickness, greater resolution is accomplished by selecting slices for treatment that are as thin as possible. As the thickness of the treatment slices decreases, the time it takes to treat the patient increases because more treatment slices are required in order to treat the entire tumor volume.

The foregoing methods and apparatus are designed to minimize the portion of the structures being exposed to radiation. However, because exposure to surrounding structures cannot be completely prevented, treatment plans are desired that are optimized to eradicate the tumor volume while minimizing the amounts of radiation delivered to the surrounding structures. Existing methods and apparatus for optimizing treatment plans use a computer to rate possible plans based on score functions, which simulate a physician's assessment of a treatment plan. However, existing methods and apparatus have proven to be insufficient.

Existing methods and apparatus utilize a computational method of establishing optimized treatment plans based on an objective cost function that attributes costs of radiation of various portions of both the tumor and surrounding tissues, or structures. One such computational method is known in the art as simulated annealing. Existing simulated annealing methods utilize cost functions that consider the costs of under-exposure of tumor volumes relative to over-exposure of surrounding structures. However, the cost functions used in existing methods do not account for the structure volumes as a whole, relying merely on costs related to discrete points within the structure, and further do not account for the relative importance of varying surrounding structure types. For example, certain structure types are redundant in their function and substantial portions of the structure volume can be completely eradicated while retaining their function. Other structure types lose their function if any of the structure is completely eradicated. Therefore, the more sensitive structure volumes can receive a measured dose of radiation so long as no portion of the structure is subjected to a lethal dose.

Existing cost functions utilized in the optimization of treatment plans do not account for such varying costs associated with the different types of structures. After the treatment plan is optimized, the physician currently must evaluate each computed treatment plan for compliance with the desired treatment objective. If the computed treatment plan does not successfully meet the treatment objectives, the optimization process is repeated until a treatment plan can be computed that meets the physician's treatment objectives for both the tumor volume and the surrounding structures. Further, existing methods and apparatus do not allow the physician to utilize the familiar Cumulative Dose Volume Histogram ("CDVH") curves in establishing the desired dose distributions.

Recent studies indicated that conformal dose distribution could be effectively achieved with the treatment technique called intensity-modulated radiation therapy (IMRT). Several promising delivery devices have also become available, such as static or dynamic MLC and tomotherapy to deliver conformal radiation dose. The basic concept of IMRT is that a dedicated delivery device with an intensity-variable modulates a uniform intensity in a traditional treatment field. However, it is still a very challenging issue in terms of how to generate an effective and optimal intensity spectrum and how to verify modulated radiation delivery. The first issue is also related to the problem of inverse treatment planning (or treatment planning optimization).

An inverse planning method describes a specific treatment planning procedure in which, differing from traditional approach, both dose and volume are given first. Then a set of modulated beams is generated through a computer-aided optimization process in order to satisfy the prescription. The process is extremely important if the shapes of the target and critical organs are complicated, especially when the target has concavity and a critical organ lies in the hollow of the concavity. Typically, inverse treatment planning for intensity modulated radiation therapy involves the selection of an objective function and method of optimization. For a given objective function, an optimal treatment plan usually requires the optimization of beam intensity elements, a prescription method, and beam number and orientation.

One of the most challenging problems in the optimization of treatment planning is how to construct a model by which the aim of radiation therapy can be fulfilled. The models that have been studied in the past can be classified as either physical or biological. There have been detailed discussions in recent literature concerning the merits and limitations of these two types of models. While biological models may be able to directly measure the clinical outcome, they still remain in the formative stages and suffer from controversy concerning the validity of the radiobiological response data used (such as, tumor control probability (TCP) and normal tissue complication probability (NTCP)). On the other hand, the physical dosimetric prescription has been well established as the clinical norm. In the traditional physical models, one optimizes an objective function that is the measure of closeness of the calculated dose distribution to the prescribed dose distribution. The crucial problem here is how to give the optimal dose value for the normal tissue so that the two objectives, delivering the desired dose to the target volume and minimizing the dose to normal tissues, can be achieved accordingly.

A quadratic model has typically being used in inverse treatment planning. The model is widely discussed and has two major limitations, no direct biological information and no minimal constraints to normal tissues. Linguistically, the purpose of radiotherapy may be stated as (a) delivering a desired tumor dose and zero dose outside the target volume; (b) delivering a high dose to the target volume and a low dose to the normal tissue. The statement (a) and (b) may be served as absolute linguistic prescription (ALP) and relative linguistic prescription (RLP), respectively. Although the ALP is ideal, it is clearly impossible to deliver due to the laws of nature. On the other hand, RLP clinically describes the strategy of radiation therapy. The words 'high' and 'low' used here are vague terms that are associated with the limitation of making precise definition. The complexity of treatment planning optimization is evident from the need to formulate some kinds of clinical goals to be optimized since there is no unique treatment plan which is clinically feasible and fulfills the two conflicting objectives: maximizing dose in the target volume while minimizing dose in normal tissues.

Recently, several researchers have paid attention to the analysis of uncertainties in radiation treatment planning optimization. The tolerance of normal tissues has been discussed. Spirou et al., developed an inverse planning algorithm with soft constraints. The method allows acceptable doses of maximum and minimum as well as dose-volume constraints to the tissues of interest.

The search for the optimal beams usually can be interpreted to be an optimization problem. Thus, the searching problem is converted to find the extremum of a given objective function. Several methods and algorithms have been investigated for inverse planning. Some examples are simulated annealing iterative approaches, as well as filtered back-projection and Fourier transformation. Although these methods are very promising, there are some aspects that can be further improved upon. The simulated annealing method may require long computation time due to the nature of random search. Most iterative approaches are parameter-dependent. The convergence and the quality of convergence may be affected by these parameters that are often determined by try-and-error. The filtered back-projection and direct Fourier transformation may have limitations on dose prescription and kernel selection. Inverse treatment planning is still at its early stage and many important aspects require be to further improved.

Additionally, Starkschall proposed an approach that removed the necessity of defining a "best" treatment plan, and incorporated the dose-volume constraints into a system to search for a feasible plan that could satisfy the constraints. If no calculated doses satisfy the treatment goal, the planner provides a guide about how the dose-volume constraints may be modified to achieve a feasible result. This approach is only applied to the conventional three-dimensional (3D) treatment planning. Wu and Mohan developed an optimization system, which employed both dose- and dose-volume-based objective functions. In the system, the optimal plan is selected by calculating the cost of the objective function, or "plan score" (the lower the score, the better the plan). Xing et al. presented a method that employed a second stage evaluation function to compute the differences between the calculated and the ideal dose volume histograms. Based on the results of the evaluation function, the weighting factors in the objective function are adjusted. The procedure minimizes both the objective and evaluation functions in a round-robin manner. Later, further improvement is achieved by using a statistical measure called preference function, which is constructed based on the empirical judgment. The problem of the selection of weighting factor still exists because it translated to the problem of how to specify the parameters in the evaluation or preference function. A similar method was also proposed by Wu et al. using a genetic algorithm to optimize the weighting factors and beam weights in the conventional 3D treatment planning. Li and Yin introduced fuzzy logic into the inverse planning system to adjust the weighting factors for normal tissue. The result was promising. However, optimizing the parameters for the target and critical organ were not included in the system. Also, the weighting factors initialized by the fuzzy functions still need to be modified by the trial-and-error approach.

It would therefore be useful to develop a method or apparatus for conformal radiation therapy, for use with a radiation beam having a predetermined, constant beam intensity for treatment of a tumor, which is simple and economical to use, has a high safety factor for patient safety, computes an optimal treatment plan to meet conflicting, pre-determined, treatment objectives of a physician, accounting for objectives in both the target tumor volume and multiple structure types, and provides the desired dose distributions for each target tumor volume and tissue and structure types.

SUMMARY OF THE INVENTION

According to the present invention, there is provided a fuzzy inference system for use in modulating radiation treatment including a fuzzifier for inputting imaging data, an inference device operatively connected to the fuzzifier, the inference device being used for analyzing the imaging data and determining radiation treatment target from non-treatment target, and a defuzzifier for modulating radiation treatment pursuant to the analysis from inference device. Also provided is a method of modulating radiation treatment by inputting patient data into the fuzzy inference system disclosed above and modulating radiation treatment pursuant to data obtained from the fuzzy inference system. An apparatus for producing modulating radiation therapy in patients including an imaging device for creating and storing image data of relevant tissue and organ parts and a fuzzy inference system operatively connected to the imaging device for modulating radiation treatment is provided. A fuzzy inference system for use in modulating radiation treatment including a fuzzifier for inputting imaging data, an inference device operatively connected to the fuzzifier, the inference device being used for analyzing the imaging data and determining strength of radiation treatment, and a defuzzifier for modulating radiation treatment pursuant to the analysis from the inference device is also provided.

BRIEF DESCRIPTION OF THE DRAWINGS

Other advantages of the present invention are readily appreciated as the same becomes better understood by reference to the following detailed description, when considered in connection with the accompanying drawings wherein:

FIG. 2A shows the membership functions "High" and "Low" defined for input variable $C_{TV}$; FIG. 2B shows the membership functions "High" and "Low" defined for input variable $C_{CO}$; FIG. 2C shows the membership functions "High" and "Low" defined for input variable $C_{NT}$; FIG. 2D shows the membership functions "Decrease", "No change", and "Increase" defined for the output variable $\Delta W_{TV}$;

FIGS. 6A and B show the variations of (FIG. 6A) characteristic doses and (FIG. 6B) weighting factors versus the iteration number in the simulated case for the dose prescription [100%, 30%, 50%], the initial weighting factors [1,1,1] were normalized to [0.58,0.58,0.58] using formula (4);

FIGS. 7A-C show the dose-volume histograms of the calculated doses in the simulated case for (FIG. 7A) the target volume, (FIG. 7B) the critical organ, and (FIG. 7C) the normal tissue for four sets of dose prescriptions;

FIGS. 8A-D show the dose distributions in the central slice of simulated case for four sets of dose prescriptions (FIG. 8A) [100%, 20%, 50%], (FIG. 8B) [100%, 30%, 50%], (FIG. 8C) [100%, 40%, 50%], (FIG. 8D) [100%, 50%, 50%];

FIGS. 9A and B show the variations of (FIG. 9A) characteristic doses and (FIG. 9B) weighting factors versus iteration number in the clinical case for the dose prescription [100%, 30%, 50%] and the initial weighting factors [1,1,1] were normalized to [0.58, 0.58, 0.58] using formula (4);

(FIG. 10A) the target volume, (FIG. 10B) the normal tissue, (FIG. 10C) the critical organ 1, (FIG. 10D) the critical organ 2, and (FIG. 10E) the critical organ 3 at iteration 5, 10, and 15, respectively.

DESCRIPTION OF THE INVENTION

Figure 1:
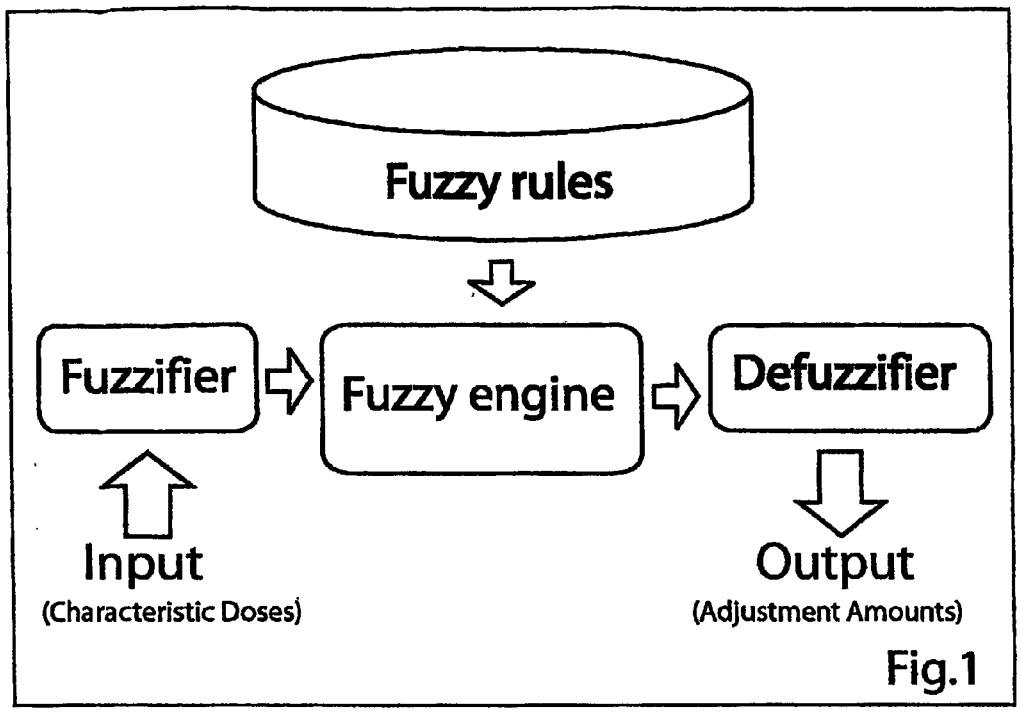
FIG. 1 shows the schematic illustration of the fuzzy inference system (FIS) used for modification of the weighting factors.

The present invention provides a method of using fuzzy logic to optimize treatments of patients. More specifically, the present invention uses a fuzzy inference system (FIS) that uses three modules: a Fuzzifier, an Inference engine that includes fuzzy rules, and a Defuzzifier. During the process of fuzzification, a single input value is compared to the membership functions as defined for that input variable. If the membership functions have a nonzero output, it will take effect in the final results of the FIS. The Fuzzifier calculates the response of rules for the input values and the inference engine modifies the consequent rules in response to input values. The Defuzzifier generates a final output based on the result of the inference engine.

The artificial intelligence (AI) method, fuzzy logic, is applied to optimize parameters in the inverse treatment planning for intensity-modulated radiation therapy (IMRT). With the capability of fuzzy inference, the parameter modification of the objective function is guided by physician's treatment intention and experience. For the different parameters involving inverse planning, the corresponding fuzzy inference systems (FISs) are developed in order to accomplish the treatment requirement. With the function of fuzzy inference, the efficiency and quality of inverse planning can be substantially improved.

The system operates in a specifically preferred manner on the basis of the so-called fuzzy-set theory approach: thus, the rules are subject to some uncertainty. The fuzzy-set theory is concerned with "fuzzy sets" whose elements belong to individual sets in different ways. While in the classical theory of sets a specific element does or does not belong to a set, the fuzzy-set theory pertains to elements that only belong to a set to a certain degree. The degree of belonging is indicated by a function for the individual elements of a set. With the approach, it is possible to make decisions based on incomplete knowledge and in the absence of exactly measured input values. Fuzzy systems are capable of operating in a stable manner even in the case of contradictory individual rules.

A fuzzy approach is developed to optimize the prescription of normal tissue. The presented method is based on the theory of fuzzy sets, and attempts to sufficiently use uncertain information under the tolerance. The method contains two types of optimizations: intensity-modulated beam optimization and normal tissue prescription optimization. The former employs the fast-monotonic descent (FMD) technique. In this technique, a new iteration method is being developed in which the update scheme is analytically determined to avoid defected convergence.

The present invention is beneficial because the heuristic and practical experience (from physician, physicist, planner) can be used to optimize the parameters of inverse planning in order to improve the dose distribution. Additionally, the conformity of target dose distribution can be improved and high target dose improves the quality of inverse planning. The time spent on trial-and-error testing can be significantly reduced and the planner can be free from this time-consuming task, thereby improving the efficiency of inverse planning.

Execution of an IMRT conformal plan using a dedicated delivery system requires accurate patient positioning. If patient is not correctly positioned, conformal radiation beams may be delivered to normal tissues rather than the planned target. Therefore, patient mis-positioning can limit the applicability of dose escalation that is the key for IMRT.

A conventional radiation field is documented by use of a portal film in a two-dimensional version. Information included in this image may not be sufficient for IMRT procedure, because the leaf position is not stationary during treatment for each field. Most quality assurance procedures for IMRT are performed in phantom. It is therefore important to find a way to verify both anatomically and dosimetrically for IMRT treatment. It has been noted that monitoring actual dose delivered in IMRT using megavoltage computed tomography (MVCT) and portal imaging taken together with transit dosimetric method grows in great importance. At present, a rapid and cost-effective method of verifying conformal IMRT radiotherapy based on limited number of fields is currently unavailable in clinical practice.

A combined method was developed to perform three-dimensional verification of patient setup and to document dose distribution treated using limited number of static IMRT fields. In this method, a megavoltage CT reconstruction technique was developed based on Multilevel Scheme Algebraic Reconstruction Technique (MLS-ART) using a megavoltage x-ray imaging device. By combining the transmitted treatment beams with the regular CT imaging projection beams, both patient geometry at treatment position and actual dose distribution can be reconstructed. The geometry and dose can be compared to the patient, setup position and prescribed dose, which are used to correct subsequent beam placement or dose delivery accordingly.

Portal CT and portal dose reconstruction is a novel verification technique in radiation therapy (especially in IMRT) with several advantages. It is online and allows direct verification of IMRT for both patient position and dose delivery. Moreover, mega-voltage CT-based technology can replace conventional patient simulation that uses kilo-voltage simulator or diagnostic x-ray CT and mega-voltage CT-based images can be used for treatment planning.

The optimization of intensity-modulated beams (IMBs) consists of two main tasks: modeling (selection of objective function) and optimization (method of minimizing objective function). In this context, modeling means that the construction of a model in which knowledge (physical, biological, and clinical) about the irradiated structure's response to radiation is expressed by an objective function. The task of optimization is to develop a method by which one can obtain the optimal solution of minimizing the objective function.

For multilateral optimization of radiation treatment planning, improving computation efficiency is an important topic. In the method of the present invention, an optimal step-length, the key parameter in the update scheme for iteration, and an optimal solution to the problem of negative intensity are analytically derived. Therefore, the convergence to global minimum is not only guaranteed, but also fast and monotonic descent. The method is called the fast-monotonic descent (FMD) method, which can provide an optimal solution to the intensity-modulated beams either when the intensity value is greater than zero or when a negative solution is encountered.

More specifically, the method functions as follows. Let $x=(x_1, x_2, \ldots, x_N)$ be an intensity vector; $x_n$ is the nth component of intensity vector x. For each dose point (i,j,k), let $P_{ijk}$ represent the prescribed dose, and $D_{ijk}$ denote the calculated dose $$D_{ijk} = \sum_{n=1}^{N} A_{n,ijk} x_n, \quad (1)$$

where $A_{n,ijk}$ is a non-negative constant coefficient that can be directly calculated. The weight $w_{ijk} \geq 0$ is used to indicate the importance of matching prescription and calculation. A quadratic objective function is therefore defined by $$f(x) = \sum_i \sum_j \sum_k w_{ijk}(P_{ijk} - D_{ijk})^2. \qquad (2)$$

In the case of an optimization problem having an objective function of Equation (2), the minimum cost problem is that of finding an admissible intensity vector such that objective function is minimized. This constrained optimization problem can be written as $$\underset{(x)}{\text{minimize}}\{f(x)\} \qquad (3a)$$

$$\text{subject to } x_n \geq 0 \ \forall \, n. \qquad (3b)$$

Now consider an unsynchronous updating scheme used in iteration method. For an arbitrary evolution time l, when $l \to l+1$, $$x_n(l+1) = \begin{cases} x_n(l) + \Delta x_n & \text{if } n = m \\ x_n(l) & \text{otherwise} \end{cases} \qquad (4)$$

and $$f(x(l)) \to f(x(l+1)),$$

where m is one of $(1, 2, \ldots, n, \ldots, N)$. The updating scheme (4) says that, for each evolution time l, only one variable is adjusted. If each of variables is adjusted one time, then it is called one cycle.

Based on the theory of classical minimum, the necessary and sufficient condition of descent for/is that the iterative rule satisfies: for each n $$\Delta x_n = -\lambda_n \frac{\partial f(x(l))}{\partial x_n}, \qquad (5)$$

where $\lambda_n$ is a small positive number and called step-length. Note that the iteration sequence generated by Equations (4) and (5) is not guaranteed to converge to the minimum of f. This convergence is always dependent upon the choice of $\lambda_n$. Adequate selection of this parameter is critical for the success of iteration method. Generally, the choice of $\lambda_n$ is a craft that is problem-specific. For a quadratic function, the parameter can be analytically derived and f will converge rapidly and monotonically to the minimum with the following condition:

$$\frac{\partial f(x(l+1))}{\partial x_n} = 0 \ \forall \, n. \qquad (6)$$

Parameter $\lambda_n$ can then be derived from the condition listed above.

$$\lambda_m = \frac{1}{2\sum_i \sum_j \sum_k w_{ijk} A_{m,ijk}^2}. \qquad (11)$$

W/th these two conditions (Eqns (5) and (6)), f descends rapidly to the global minimum if for each m $(1 \leq m \leq N)$ $$x_m(l+1) = \begin{cases} x_m(l) + \sum_{n=1}^{N} B_{mn} x_n(l) + C_m & \text{if } x_m(l+1) > 0, \\ 0 & \text{otherwise;} \end{cases} \qquad (7)$$

where l denotes the l-th iteration, $$B_{mn} = -\frac{\sum_i \sum_j \sum_k w_{ijk} A_{m,ijk} A_{n,ijk}}{\sum_i \sum_j \sum_k w_{ijk} A_{m,ijk}^2},$$

and $$C_m = \frac{\sum_i \sum_j \sum_k w_{ijk} A_{m,ijk} P_{ijk}}{\sum_i \sum_j \sum_k w_{ijk} A_{m,ijk}^2}.$$

The FMD algorithm can be summarized as follows:
1) Fix the maximum number of iterations L, weights $\{w_{ijk}\}$, and termination criterion $\epsilon > 0$.
2) Initialize $x(0) = (x_1(0), x_2(0), \ldots, x_N(0))$, and $x \geq 0$ for each n.
3) For l=1, 2, . . . , L;
   a. Update intensity vector using Equation (4).
   b. Compute $$E_l = \max_{\{n\}} \|x_n(l+1) - x_n(l)\|.$$

c. IF $E_l \leq \epsilon$ stop; ELSE next l.
4) Compute dose distribution using Equation (1).

f is a constrained quadratic objective function. A set of values $x_1, x_2, \ldots, xN$ that satisfies the non-negative constraints expressed by Equation (3b) is called an admissible vector, and the admissible vector that minimizes the objective function is called the optimal admissible vector. An optimal admissible vector can fail to exist for two reasons. There are no admissible vectors (i.e., the given constrains are incompatible) or there is no minimum (i.e., there exists a direction in N space where one or more of the variables can be taken to negative infinity while still satisfying the constraints). Fortunately, neither of them is satisfied in the problem of intensity-modulated beam optimization. First, it is clear that, the sets in Equation (3b) are convex, and the intersection consists of many points. Therefore, the non-negative constraints in Equation (3b) are compatible. The second reason is also false, since the intensity variables are non-negative.

There is one important parameter $\{W_{ijk}\}$ in Equation (2) that has not been addressed above. Typically, the prescribed dose for the target volume and the upper limit for the sensitive organ is known. The prescription for the normal tissue is usually not given. Therefore, the optimization result varies with the prescription selected for the normal tissue. An intuitive strategy for finding the optimal normal tissue prescription would be to compare values of objective function calculated by using different prescribed doses and then to choose the minimum. In this way, $w_n$, the weight for the normal tissue, is a function of $p_n$, the prescribed dose for the normal tissue. Here, the subscript n represents a point (i, j, k) inside the normal tissue. The difficulty of using this strategy is how to formulate the relationship between weight $w_n$ and prescribed dose $p_n$. Generally, all that is known is a plausible relationship between them: $w_n$ is the least when $p_n$ approaches to zero and $w_n$ is the greatest when $p_n$ approaches to the upper limit. A dynamic weight function is used to express this fuzzy relationship. An optimal prescription dose for normal tissue is then determined by a validity function.

A quadratic objective function, as shown in Equation 2, with fuzzy weight as $$P_{ijk} = \begin{cases} p_t, & \text{if } i, j, k \in \Omega_t \\ p_s, & \text{if } i, j, k \in \Omega_s \\ p_n; & \text{if } i, j, k \in \Omega_n \end{cases}$$

and $$w_{ijk} = \begin{cases} w_t, & \text{if } i, j, k \in \Omega_t \\ w_s, & \text{if } i, j, k \in \Omega_s \\ w_n. & \text{if } i, j, k \in \Omega_n \end{cases}$$

$p_t$, $p_s$ and $p_n$ denote the prescribed doses for the target volume, the sensitive organ and the normal tissue, respectively $\Omega_t$, $\Omega_s$ and $\Omega_n$ represent regions of these three corresponding structures. $W_{ijk} \in [0,1]$ is called fuzzy weight function that is used to emphasize the importance of matching the prescribed dose and the calculated dose for the point (i, j, k). Instead of fixing $\{P_{ijk}\}$ and $\{w_{ijk}\}$ in the hard inverse planning (HIP), $p_n$ is defined as a variable and $w_n$ is represented by a function of $p_n$ in fuzzy inverse planning (FIP). Also, it is assumed that $$p_t = P_t, \; p_s = P_s, \; w_t = w_s = 1 \quad (9)$$

and $$w_n = \begin{cases} 1, & \text{if } p_n > P_n \\ g(p_n), & \text{otherwise} \end{cases}$$

where $P_t$ represents the prescribed dose in the target volume, $P_s$ is the tolerance dose in the sensitive organ, and $P_n$ is the tolerance dose in the normal tissue. $g(p_n)$ is a continuous function that increases with $p_n$. $g(p_n)=1$ when $p_n$ is equal to the tolerance dose $P_n$. Here $g(p_n)$ is called fuzzy weight function.

Regarding the function $g(\cdot)$, one has only some vague knowledge that can be stated by the following two fuzzy rules: 1) the closer $p_n$ is to $P_n$, the closer $w_n$ is to one ($w_n=1$ means the most important); 2) the closer $p_n$ is to zero, the closer $w_n$ is to zero ($w_n=0$ means the least important). Fuzzy technology is used to express the vague knowledge and to achieve an optimal solution. The form of fuzzy weight function can be obtained from a planner's experience. As will be seen below, however, it is effective to use the following function:

$$g(p_n) = \left(\frac{p_n}{P_n}\right)^K, \quad (10)$$

$$0 \leq p_n \leq P_n$$

where K is a positive constant that controls the pattern of $g(\cdot)$. These functions are shown in FIG. 1. Obviously, any function with a K value of equal to or greater than 1 can be selected to express the mathematical meaning of the following linguistic prescription. For the normal tissue, the closer the prescribed dose $p_n$ is to the tolerance dose, the greater the importance of the dose (i.e., the difference between the tolerance dose and the prescribed dose).

Fuzzy inverse planning allows many feasible solutions to occur for a specific clinic problem. Selection of a specific treatment plan is determined by evaluating planning validity. Note that Equation (8) cannot be served as a validity function since the objective of radiation therapy optimization for non-target volume cannot be expressed by a quadratic function. To measure the validity of radiation treatment, a validity function is introduced, $v(\{P_{ijk}\};x)$, which is written as $$v(\{P_{ijk}\}; x) = \sum_{i,j,k \in \Omega_t} |P_{ijk} - D_{ijk}| + \sum_{i,j,k \notin \Omega_t} D_{ijk}. \quad (11)$$

where, the first term represents the degree of dose uniformity for the target volume, and the second term represents the grade of protection of the non-target volume. For prescription validity, the ideal dose distribution can be achieved by minimizing $v(\{P_{ijk}\};x)$ under the tolerance of normal tissues:

$$\text{minimize}\{v(\{P_{ijk}\};x)\}. \quad (12)$$

With the introduction of this validity function, the fuzzy inverse planning (FIP) algorithm can be summarized as follows. Fix the maximum number of trial dose prescriptions T for normal tissue, the maximum number of iterations L, and the termination criterion s>0. Choose fuzzy weight function $g(\cdot)$. Initialize $x(0)=x_1(0), x_2(0), \ldots, x_N(0))$, and $x_n \geq 0$ for each n. Then, for t=1, 2, ..., T, given $p_n$ (usually $p_n$ increases with t on the interval $(0, P_n)$, calculate $w_n$ using Equation (9), for l=1, 2, ..., L and update intensity vector using Equation (7), compute $$E_l = \max_{\{n\}} \|x_n(l+1) - x_n(l)\|.$$

if $E/\leq \epsilon$, calculate v using Equation (11), otherwise next l. IF $v_{t+1} > v_t$ stop, otherwise next t. The dose distribution can then be computed using Equation (1).

Preferably, a computer is utilized to automatically calculate this in response to the input of data, however, a human can also calculate the same using the formula.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein. The FIP is evaluated by two artificial examples. Dose-volume histograms (DVH) of the target volume (TV) and the sensitive organs (SO) are used as a primary tool for presenting and comparing dose distributions.

EXAMPLES

Example 1

Figure 2:
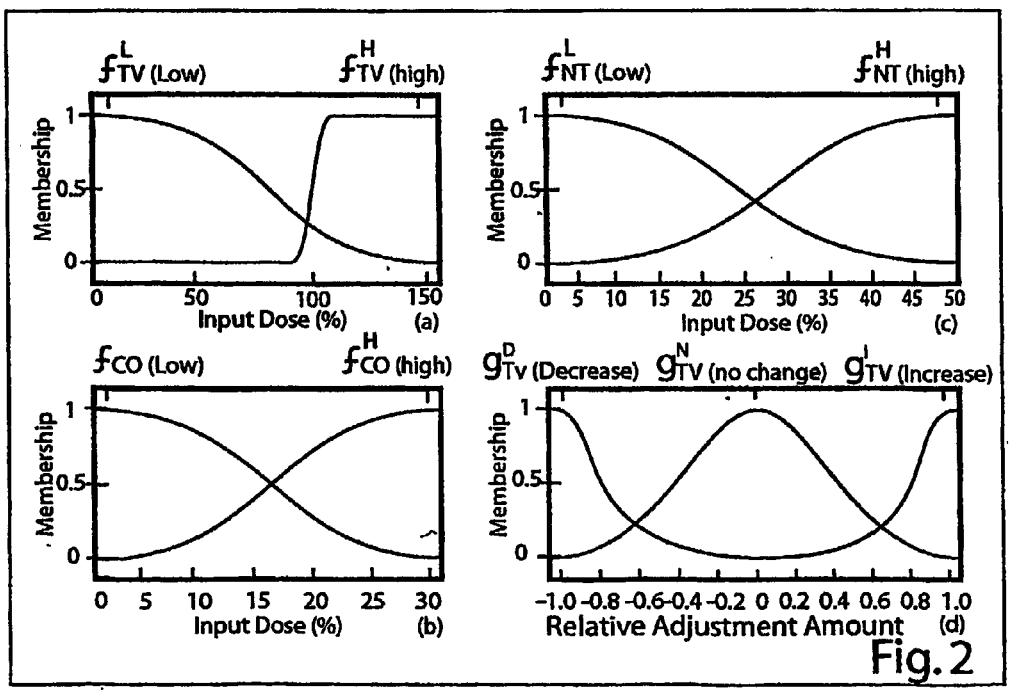
FIGS. 2A-D are illustrations of membership functions used in FIS.

This is a simulated cylindroid object and its central slice is illustrated in FIG. 2. The geometry of this slice is similar to a CT head axial cut with two sensitive organs (analog to eyes) that are very close to the target volume. The prescription was given as follows: 100 dose units to the target volume, 20 dose units to the sensitive organs, and upper limit of 60 dose units to the normal tissue. Seven fan beams as shown in FIG. 2 were uniformly arranged between 0-2 π. Based on the primary-only model, the dose at depth is estimated by means of the percent depth dose data that were measured from a field size of 4×4 cm with 6 MV photon beams. However, beam divergence was included.

Figure 3:
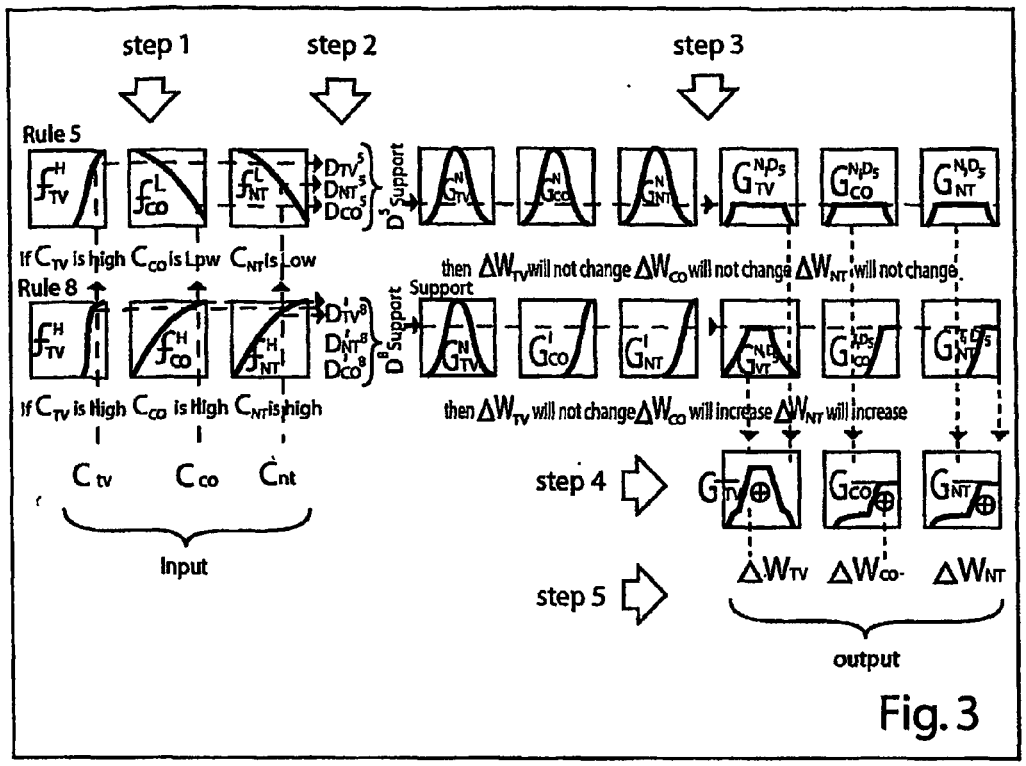
FIG. 3 shows the demonstration of the inference procedure including the following steps: Step 1: Inputs fuzzification; and Step 2: Degree of support; Step 3: Fuzzy inference (implication operation); Step 4: Aggregation operation; and Step 5: Output defuzzification.
Figure 4:
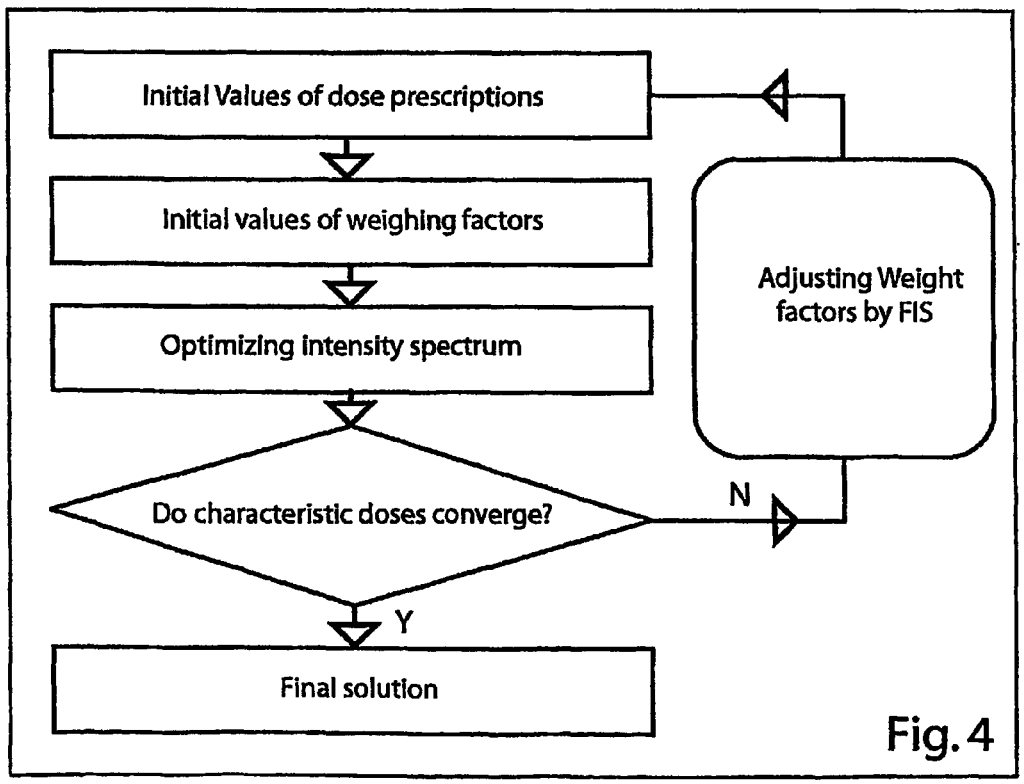
FIG. 4 shows the flow chart of the fuzzy logic guided inverse treatment planning system.

In order to show the convergence and fastness of FMD method, the FMD algorithm was run using three different values of the step-length: $\lambda_n=0.01$, $\lambda_n=\lambda_{opt}$ and $\lambda_n=0.001$ (n=1, 2, ..., N). Here $\lambda_{opt}$ is the optimal step-length. FIG. 3 shows the differences of convergence behavior between $\lambda_n=\lambda_{opt}$ and $\lambda_n=0.001$, and between $\lambda_n=\lambda_{opt}$ and $\lambda_n=0.01$ (n=1, 2, ..., N). The result indicates that the effectiveness of iteration methods is dependent upon the choice of step-length. The optimal step-length $\lambda_{opt}$ derived here, however, provides an optimal performance in both the speed of convergence and the quality of convergence. FIG. 4 shows that FMD can provide a satisfactory result after 10 cycles.

Effect of Normal Tissue Dose

In the study, a validity function is introduced to judge the optimal normal tissue prescription. Variation of validity function v versus prescribed normal tissue dose is plotted in FIG. 5. The data in FIG. 5 indicated that $p_n=25$ dose units appear to be the optimal prescription for normal tissue. Table 1 shows the fuzzy inverse planning (FIP) performance as a function of the normal tissue prescription dose with K=5 and L=100. Here $p_n=0$ means no normal tissue is considered in the FMD optimization algorithm, i.e., $w_n=0$ and $w_s=w_t=1$. Although statistic indices for the target volume in the case of $p_n=0$ are better than others, the average dose of 52.6 dose units and the standard deviation of 33.8 dose units for the normal tissue far exceed the upper limit of 60 dose units. The data listed in Table 1 show that the optimal balance between objectives of high target dose and low normal tissue dose is achieved when $p_n=25$ dose units. FIG. 6 shows corresponding dose-volume histograms for the target volume (FIG. 6(a)), the sensitive organs (FIG. 6(b)) and the normal tissue (FIG. 6(c)). The improvement of performance is evident with the optimization of normal tissue dose prescription.

Comparison of FIP and HIP Methods

The case described above, with a normal tissue dose prescription of 25 units, can be considered an optimal result for the FIP algorithm: In this section the result obtained by the FIP method is compared to that obtained by the hard inverse planning (HIP) method. HIP means that only the FMD algorithm is applied. For the HIP method, two extreme prescriptions are selected: (a) no normal tissue is considered in the optimization algorithm, i.e., $w_n=0$ and $w_s=w_t=1$; (b) the prescribed normal tissue dose is fixed, i.e., $p_n=P_n=60$ and $w_n=w_s=w_t=1$.

Dose-volume histograms are calculated and illustrated in FIG. 7(a) for the target volume obtained using FIP, HIP(a), and HIP(b), respectively. Corresponding dose-volume histograms for the sensitive organs and the normal tissue are illustrated in FIG. 7(b) and FIG. 7(c). Table 2 provides the relevant statistical parameters. It has been shown that the overall results obtained by optimizing prescription of normal tissue dose (FIP method) are better than those obtained by HIP(a) and HIP(b).

Effect of Parameter K

As discussed in Section III, validity function g(•) is considered to be adequate if K=1. The effect of the parameter K in Equation (10) on the performance of FIP method is evaluated by using values of K=1, 2, ..., 5. Dose-volume histograms obtained using different K values for the target volume (FIG. 8(a)), the sensitive organs (FIG. 8(b)), and the normal tissue (FIG. 8(c)) are calculated and compared. Results indicated that the uniformity of dose for the target volume is improved as K increases. At the same time, the control of dose for the sensitive organ is stronger as K increases. However, the control of dose for the normal tissue is weaker as K increases. Therefore, the result of K=5 is more desirable than those of others are. If K is greater than 5, the performance of normal tissue would be less desirable despite of dose improvement in other structures.

Example 2

The central slice of the phantom geometry in Example 2 is illustrated in FIG. 9. Similar to Example 1, seven fan beams are arranged at 0, 2 π/7, 4 π/7, 6 π/7, 8 π/7, 10 π/7, and 12 π/7, respectively. The prescribed doses were set: 100 dose units for the target volume, 20 dose units for the sensitive organs and the upper limit dose of 60 dose units for the normal tissue. The other parameters were L=100 and K=5.

Figure 10:
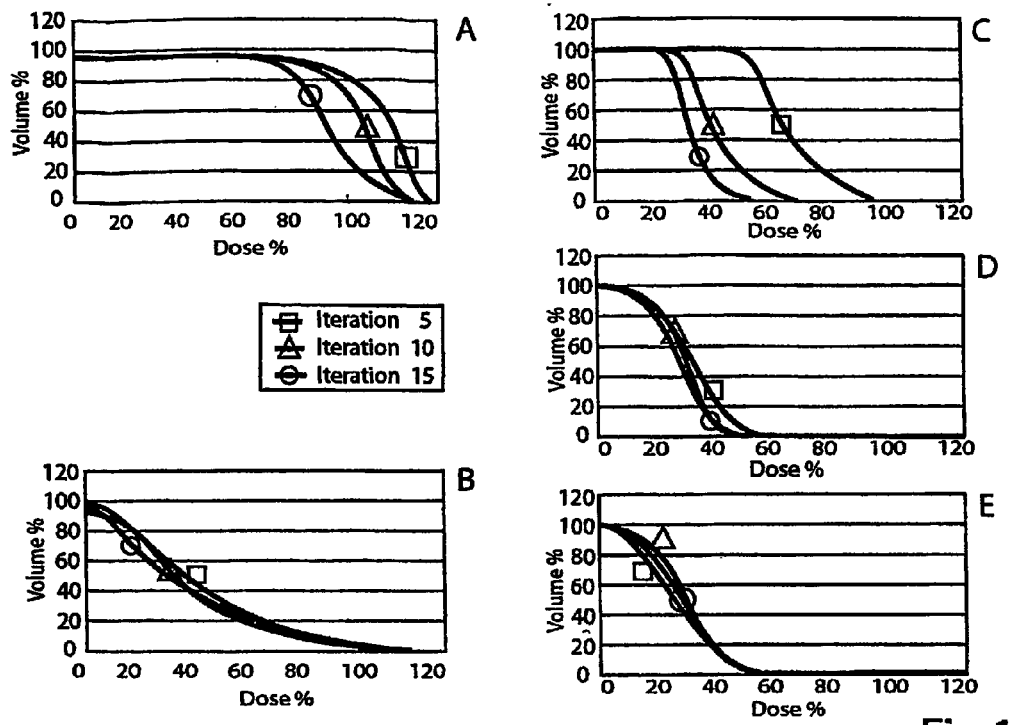
FIGS. 10A-E show the dose-volume histograms of calculated dose distributions for five involved organs.

FIG. 10 shows dose-volume histograms obtained by using FIIP, HIP(a) and HIP(b) methods for the example 2. FIG. 10(a) corresponds to the target volume, FIG. 10(b) to the sensitive organs, and FIG. 10(c) to the normal tissue. Table 3 indicates the relevant statistical parameters: means, standard deviations for the three structures in Example 2. The performance patterns of the FIP algorithm in Example 2 is consistent with the results obtained in Example 1. However, the optimal normal tissue value $p_n$ here is equal to 30. Note that in this example one can also obtain a desirable result without considering normal tissue, i.e., FIP has similar result as HIP (a).

Megavoltage CT Image Using Limited Number of Projections

The use of a fluorescent/CCD-based EPID, coupled with a novel Multilevel Scheme Algebraic Reconstruction Technique (MLS-ART), was analyzed for a feasibility study of portal CT reconstruction (Ying 1990, Wong 1990, Yin 1994, Zhu 1995). An EPID set it to work at the linear dynamic range and collimated 6 MV photons from a linear accelerator to a slit beam of 1 cm wide and 25 cm long was used. Scans were performed under a total of 200 MUs for several phantoms in which the number of projections and the MUs per projection were varied. The reconstructed images demonstrated that using the new MLS-ART technique, megavoltage portal CT with a total of 200 MIUs can achieve a contrast detectability of 2.5% for an object of size 5 mm×5 mm and a spatial resolution of 2.5 cm.

Using a CsI(T1) transparent scintillator x-ray detector together with the multi-level scheme algebraic reconstruction technique (MLS-ART) for megavoltage computed tomography (CT) reconstructions. The reconstructed CT images can be useful for positional verification in radiotherapy. The Csl (T1) imaging system consists of a scintillator screen coupled to a liquid-nitrogen-cooled slow-scan CCD-TV camera. The system provides better contrast resolution than the standard electronic portal imaging system (EPID), which is especially useful given the low number of projections used. The geometry of the imaging system has also been optimized to achieve high spatial resolution (1 lp/mm) in spite of the thickness of the screen. The reconstructed images were presented using a pediatric head phantom using a total of 99 projections, and a combined phantom using 50 projections. Image reconstruction was carried out using the MLS-ART technique. The CT images obtained using the back projection technique for comparison purposes were also presented.

In addition, the use of the kinestatic charge detector (KCD) combined with the multi-level scheme algebraic reconstruction technique (MLS-ART) for x-ray computer tomography (CT) reconstruction was also investigated. The KCD offers excellent detective quantum efficiency and contrast resolution. These characteristics are especially helpful for applications in which a limited number of projections are used. In addition, the MLS-ART algorithm offers better contrast resolution than does the conventional convolution backprojection (CBP) technique when the number of projections is limited. Here the images of a Rando head phantom that was reconstructed by using the KCD and MLS-ART were presented. Also presented, for comparison, the images reconstructed by using the CBP technique. The combination of MLS-ART and the KCD yielded satisfactory images after just one or two iterations.

The advantages of MLS-ART applied to conformal radiotherapy are following:

a. The MLS-ART outperforms the conventional CBP technique for low contrast detection given a limited number of projections and it is especially useful for megavoltage CT reconstruction since in radiotherapy one cannot rotate the linear accelerator gantry to acquire a large number of projections in a reasonably short of time. Contrast detectability is strongly dose-dependent, and for some situations in x-ray imaging, high contrast resolution is not as important as the ability to provide excellent image contrast (Yaffe and Rowlands 1997). Such is the case with megavoltage CT imaging for radiation treatment verification. The high-energy x-ray photons experience inherently low attenuation in tissues. In addition, attenuation of radiation by tissues in the energy range is mainly due to Compton scattering that depends on electron density but not the atomic number. The two factors combined resulted in poor differentiation between various tissues (Johns and Cunningham 1983). Further, the detective quantum efficiency (DQE) of current megavoltage imaging devices is at least one order lower than those of detector for diagnostic x-ray CT. Therefore, megavoltage portal CT requires an efficient reconstruction technique like the MLS-ART, especially the one that is optimal for situations of low-contrast detectability. Better contrast detectability also helps for more accurate dose reconstruction since spatial resolution imposed on dose is even more relaxed.

b. MLS-ART can be used for CT reconstruction using the radiation treatment beams in addition to the regular CT projection beams. Such a 2-step reconstruction produces much better reconstruction accuracy than simply using the treatment beams themselves because the latter is a case of incomplete data (although even for this case, MLS-ART itself works better than CBP.) In this way, the patient position can be directly and continuously monitored and even corrected during the treatment.

c. Doing conformal radiotherapy using intensity modulated beams and portal CT is complicated by the tumor irregularity. Depending on the target shapes and sparing of critical organs, select treatment beam orientations to be orthogonal or close to orthogonal are important. The orientations must yield small geometrical correlations (less dose overlap) and most complementary dose distribution information. One can select the beam orientations following the MLS ordering, or in combination with methods known to those of skill in the art, such as the methods used by Gokhale, Soderstrom, Bortfeld.

d. MLS-AIRT can be used for dose reconstruction. It is more accurate than the analytical method given a limited number of beams because for any analytical dose integration method, there is an implicit assumption that an infinite number of projections were used. But the integration method fails if the angles between beams are large unless special techniques like arc therapy for tomotherapy are used.

Reconstruction of IMRT Beams for Dose Distribution

Methods:

Inverse Treatment Planning Algorithm for IMRT:

Research Method:

First, it should been pointed out that the definition of fuzzy weight function as shown in Equation (10) is not a unique form. Different functions can be used to achieve different goals. The Gaussian function was tested instead of Equation (10) and it was found that the result obtained using Equation (10) is better than that obtained using a Gaussian function. Second, in the present study two loss functions are introduced. One is the objective function as shown in Equation (8) and the other is the validity function as shown in Equation (11). The former is used to optimize beam intensity. The latter is employed to evaluate the prescription of normal tissue. The objective function as shown in Equation (8) cannot replace the validity function as shown in Equation (11). For example, it is equal important in terms of loss value when the calculated dose in normal tissue is either 10 below or 10 above the prescribed dose. Therefore, Equation (8) does not completely express the objectives of radiotherapy, and a validity function as shown in Equation (11) is necessary. In addition, it is clear that Equation (11) is an unbiased measure function since the loss for the non-target volume is calculated from zero.

In the present study there is described a fuzzy inverse planning (FTP) method for solving the problem of uncertain prescription optimization in radiation therapy. The study is concerned only with the optimization of normal tissue prescription. The dose prescription in the sensitive organs is fixed. Typically, the upper limit dose for the sensitive organ is less than that for the normal tissue. It is difficult to control the calculated dose less than the upper limit for the sensitive organ (except for those cases in which the sensitive organs are far from the target volume). Typically, the mean dose in the sensitive organs is greater than the upper limit dose. The importance of matching the calculated dose and the prescribed dose for the target volume is equal to that for the sensitive organ, i.e., $w_t = w_s = 1$. Clinically, it means that the importance of protecting the sensitive organ is the same as that of controlling the tumor. However, different weighting factors can be chosen by radiation oncologists for a specific clinical case to fulfill a special objective.

A fuzzy inverse treatment-planning algorithm has been developed. The method provides an alternative to soft optimization for treatment planning. The main advantages have two folds. (a) The developed FMD has the fastest convergence speed in the stage of optimizing the beam intensity and the algorithm is simple to use in which no parameter is problem-specific. And (b) the FIP technique can use uncertain information in inverse treatment planning to achieve the optimal balance between the objectives of matching the calculated dose and the prescribed dose for the target volume and minimizing the dose in normal tissue. The presented technique optimizes not only beam intensity distribution but also normal tissue prescription. The performance of the new algorithm has been compared to that of the hard, inverse planning methods for two treatment geometries. The calculation time is less than 2 minutes on PC machine (333 mHz, 64 MB RAM) for 10 slices with a matrix size of 256×256. At the present, it is difficult to compare between different approaches due to difference in test cases, dose calculation and other factors.

Inverse planning method involves two key components: objective function to define the goal for the optimization, and optimization method to find the optimal solution for a given objective function. The optimization algorithm developed here may be also applicable to resolve objective functions based on biological model.

$$f(x) = \sum_i \sum_j \sum_k w_{ijk}(P_{ijk} - D_{ijk})^2$$

The physical meaning of $W_{ijk}$, $P_{ijk}$, and $D_{ijk}$ are as described above.

Optimization Method

Compared to some existing iteration techniques, there are several unique characteristics of FMD technique. (1) The key parameter, step-length, used in update scheme is analytically calculated so that no trial-and-error is involved. Choice of update scheme is critical for fast convergence and optimal results. Inappropriate selection of the step-length may lead to poor convergence or even non-convergence. (2) Fast and monotonically convergence guarantees the global minimum of the optimization algorithm. (3) The problem of negative beam intensities is effectively eliminated. (4) The algorithm is simple to understand and implement for clinical applications.

Fuzzy Representation of Vague Prescription

The concept for a logistic plan is to deliver full dose to the target region while keeping the dose below the maximum tolerance for normal tissues. The quadratic model in the above section is not sufficient to address the upper limits for normal tissue prescription. A fuzzy function was introduced to represent vague normal tissue prescription.

The theory of fuzzy set is a mathematical tool used to represent uncertain or partial knowledge. In inverse treatment planning, one only knows the upper limits for normal structures but is not certain what is the optimal prescription, especially the prescription for normal tissue and critical organs. Therefore, the category of problem can be represented by the theory of fuzzy set.

The objective function can be divided into three terms. The first term relates to the target volume that is expected to receive uniform prescription dose. The second term relates to the critical organs that are sensitive to radiation damage and a tolerance dose will be set. The third term relates to the normal tissues except critical organs in which dose is expected to be as low as possible. To achieve these goals, the weight factors in the objective function can be redefined as follows:

$W_{ijk}$ in target volume wt=tt, where tt is a constant and is used to indicate the importance of matching target dose. Typically, tt=1.

$W_{ijk}$ in critical organs $w_c$=cc*h($p_c$,$P_c$), where cc is a constant and is used to indicate the importance of matching prescription for each critical organ.

$W_{ijk}$ in critical organs $w_n$=nn*g($p_n$,$P_n$), where nn is a constant and is used to indicate the importance of matching prescription for normal tissues.

Here both g and h are two fuzzy functions. The fundamental of constructing a fuzzy function is to find proper weighting factors in the objective functions. Linguistically, the closer the prescribed dose is to the tolerance dose, the greater the importance of the dose (i.e., the difference between the tolerance dose and the prescribed dose). Mathematically, it can be described by a following function:

$$g(p_n) = \left(\frac{p_n}{P_n}\right)^K, \quad 0 \le p_n \le P_n \quad (10)$$

$$h(p_c) = \left(\frac{p_c}{P_c}\right)^K, \quad 0 \le p_c \le P_c \quad (10)$$

where K is a positive constant that controls the patterns of g(•) and h(•) These functions are shown in FIG. 1. Obviously, any function with a K value of equal to or greater than 1 can be selected to express the mathematical meaning of the following linguistic prescription.

Penalty of Optimization Method

Fuzzy inverse planning allows many feasible solutions to occur for a specific clinic problem. Selection of a specific treatment plan is determined by evaluating planning validity. Note that Equation (8) cannot be served as a validity function since the objective of radiation therapy optimization for non-target volume cannot be expressed by a quadratic function. For example, when the calculated dose is greater than (but closer to) the prescribed dose, the objective function will not able to penalize such a situation. To measure the validity of radiation treatment, a validity function is introduces, say $v(\{P_{ijk}\};x)$, which is written as $$\sum v(\{P_{ijk}\};x) = tt \sum_{i,j,k \in \Omega_t} |P_{ijk} - D_{ijk}| + nn \sum_{i,j,k \notin \Omega_t} D_{ijk} + cc \sum_{i,j,k \notin \Omega_t} D_{ijk} \quad (11)$$

The importance of requiring the quadratic function is that it is proved that the global minimum does exist and is unique. Here tt, nn, and cc are used to indicate the importance of matching each term. The parameters can be determined by the planner based on the clinical needs for each individual patient. When an equal importance is reached, tt, nn, and cc are equal to 1. If DVH is used to judge the results, tt, nn, and cc can be used changed to reach final plan.

Evaluation of Inverse Planning Method:

Phantom Test

The developed inverse planning method was tested with three cylindrical, phantoms: brain, head and neck, and pelvis. Each geometry has both complicated target volume and critical organs around it. The primary beam was acquired from TMR data for 4×4 cm field size of 6 MV photon beam.

Patient Case Test

IMRT Experiment

Clinical implementation was based on step-and-shot approach including the following:
a. patient CT image;
b. input to Pinnacle 3-D planning system;
c. contour target and critical structure and external edges;
d. export contours and CT images to inverse planning algorithm;
e. generate IMRT intensities for each beam;
f. segment each beam for step-and-shot;
g. import segmented field to Pinnacle 3-D system; and
h. calculate MIUs for each segment.

Three-Dimensional Reconstruction of Dose Distribution

With the patient at the treatment position, the same projection data for the geometry reconstruction was used to estimate the true dose delivered to the patient. A scheme for 3-D dose verification was developed, which requires overlaying the reconstructed patient geometry at treatment with the distribution of the delivered dose. This serves as a verification tool to the initial treatment planning.

In the current megavoltage CT imaging, a uniform beam was used for both the calibration runs and the projection measurements. For the EMIRT, the x-ray beam from each projection was modulated in intensity, i.e., non-uniform. Therefore, the IMRT beams were measured before the patient is placed in the treatment room to get the entrance intensity distribution. An alternative way was to download the distribution from the IMRT delivery files; however, this option is less direct than measurement. Without these entrance beam intensity, one would be unable to decide whether any exit intensity change is due to the entrance intensity change or different attenuation within the patient geometry. Image reconstructions using the intensity-modulated beam can be tested initially using simply compensator or wedge.

Different patient dose calculation methods can be used based on the measured transmission x-rays (most of the detected x-rays are primary components for that there is a 50 cm air gap between the patient exit surface and the detector. The scatter fraction for a 20×20 field size, 17 cm thick water and 30 cm air-gap is 10% [Jaffray et al., 1994]). The first two methods are based on the primary photon fluences at the point of dose calculation. These are called the convolution-superposition and the superposition-convolution method. In the first method, the x-ray fluence at the detector surface is ray-traced back to inside the patient's geometry. The fluence can be convoled inside the patient with an appropriate energy deposition kernel (dose spread array) to obtain the dose distribution. By superimposing all the distributions over the reconstructed patient geometry, one can obtain the total dose distribution. In the second method, first, the x-ray fluences of all the beams at the detector surface are ray traced back and superimposed together to get the total primary x-ray fluence distribution inside the patient. Then one can convolve the total fluence distribution with a rotation dose spread kernel to get the total dose distribution. In both methods, normalization (calibration) is needed. The third method is based on the primary photon distribution attenuated inside the patient. The overall primary attenuation distribution in the patient, which is different from the total primary fluence ray traced back from the detected x-rays, can also be reconstructed, using the similar methods for the emission tomographic reconstructions such as PET and SPECT. (For each beam the attenuation profile was obtained by subtracting the penetrated primary from the entrance beam.) Then, the overall attenuation distribution was convolved with a special rotation dose kernel (which is calculated based on the photon numbers rather than the photon fluence) to get the dose distribution. MLS-ART can be applied for such a photon attenuation reconstruction (with some modification) based on the experiences of Herman [1993], but not the conventional CBP technique due to the limited beam numbers. Further, the homogeneity corrections can be directly calculated based on the geometric reconstructions. Compared to the first two methods, the third method is more direct, accurate and convenient. It is also easier for the intensity-modulated beams. With faster and growing computation technology including hardware specifically designed for MLS-ART and FFT, one can achieve faster and more accurate on-line verification.

To be more accurate, one needs to calculate the primary fluence on the detector's surface by deconvolving the projection data (measured during treatment session, therefore no additional dose to the patient) using the "EPIID kernel" (the point spread function of EPD).

One can also use some portal dosimetry methods to model the exit dose distribution and to compare it to the calculation results. It can also be used to model the absorbed dose inside the treatment volume (actually the dose along the beam path) based on the treatment geometry as reconstructed using the MLS-ART. The results were compared to some other dose modeling and verification methods such as the portal dose imaging (PDI) technique [Wong et al., 1990], the superposition/convolution method [McNutt et al., 1996a & b], and the inverse filtered (convolution) back-projection method of Holmes and Mackie [1994].

The other advantage of using the C51(T1) detector for dose modeling and verification throughout the treatment volume is that compared to commercial EPID which overrespond to low energy x-rays for dosimetry studies, the detector is more tissue equivalent. If a-Si detector is used, a more active way to reduce over-response is to use organic scintillators (low-Z plastic materials) on the detector so that detector response will be more tissue equivalent. One way is to use a low-Z screen with a buildup phantom such as the solid water. Then the photons undergo interactions in the buildup material. The secondary electrons are mainly absorbed in the organic screen, and the visible photons are emitted toward the a-Si photodiode sensor. The merit of using such an organic screen is that the dose deposition by electrons inside the tissue can be exactly modeled by using the tissue-equivalent organic material. The screen needs to be fabricated by a medical imaging company because the currently available screen has poor surface smoothness.

For clinical application of megavoltage portal CT, improving the accuracy of reconstruction rests on more efficient detectors and optimized reconstruction algorithms to most effectively use the available dose. In the study, three interrelated specific goals can be analyzed.

(1) Adapt an efficient x-ray detector to carry out the study. There are 3 options: a) use Varian Portal Vision Electronic Portal Imaging Device (EPD), which tested to be the best commercial EPID system; b) use the amorphous silicon system; and c) use a C5I(T1) CCD system which was specifically designed for megavoltage imaging. The CsI(T1) system is one of the best megavoltage imaging systems, providing both good contrast and spatial resolution.

(2) Image reconstruction. The MLS-ART technique can be used for this specific application, in which a limited number of cone beam projections (dosage close to that in diagnostic CT) are used to get megavoltage CT reconstruction for patient geometry. Then the treatment beams can be used to further modify the reconstruction. The two-step reconstruction has three important purposes: 1. the second stage locally improves the CT image quality inside the tumor; 2. the second stage also determines the placement of treatment beams inside the patient geometry obtained by the first step; and 3. the treatment (dose covered) area can be visualized from the final CT images. MLS-ART can easily perform the reconstruction. However, it is impossible for the conventional convolution backprojection (CBP) technique.

(3) Dose reconstruction and verification. From the portal image taken at the treatment portal, one can obtain the portal (transit) dosimetry and convert the portal dose information to photon fluence. The fluence can be traced back to the patient and one can determine the fluence inside the target. The convolution-superposition or superposition-convolution or other methods can then be used to calculate the dose inside the patient use the fluence. Such a 3D dose distribution can be overlaid onto the patient geometry to verify the treatment plan. Any major discrepancy between the prescribed and actual dose can be corrected by modification of the treatment setup.

Example 3

Materials and Methods

For a given dose prescription, conventional inverse treatment planning consists of two steps: (1) finding the suitable weighting factors for involved organs and (2) optimizing the intensity spectrum based on the given weighting factors. As there are a large number of choices for weighting factors, finding the desired ones for a given objective function is difficult. The involved organs in this system are categorized as the target volume (TV), the critical organs (CO), and the normal tissue (NT).

The Principle of the Fuzzy Inference System

The flow chart of FIS is illustrated in FIG. 1. It consists of three main modules: the Fuzzifier, the Inference Engine (consisting of fuzzy rules) and the Defuzzifier. For each variable input to the fuzzy inference system, a number of fuzzy sets are defined with appropriate membership functions. These membership functions are labeled with linguistic tags frequently used by humans (such as "High" dose). During the process of fuzzification (corresponding to the module of Fuzzifier), the single input value is compared to the membership functions defined for that input variable. If the membership functions have a non-zero output, it will take effect on the final result of the FIS. Generally, the fuzzifier calculates the response of rules for the input values, and the inference engine modifies the consequent of rules in response to the input values and the defuzzifier generates the final output based on the result of the inference engine.

The inputs to this system are defined as the characteristic doses $[C_{TV}, C_{CO}, C_{NT}]$ which consist of the mean dose (Mean$_i$, i=TV, CO, NT) and its standard deviation (STD$_i$, i1=TV, CO, NT). For the target volume, $C_{TV}$=Mean$_{TV}$−STD$_{TV}$. For the critical organs and normal tissue, $C_{CO}$=Mean$_{CO}$+STD$_{CO}$ and $C_{NT}$=Mean$_{NT}$+STD$_{NT}$. The outputs of FIS $[\Delta W_{TV}, \Delta W_{CO}, \Delta W_{NT}]$ are defined as the adjustment of the weighting factors for each involved organs. For each input variable, two fuzzy sets, "High (H)" and "Low (L)", are defined with membership functions $[f_i^H(x), f_i^L(x), i=TV, CO, NT]$, as shown in FIGS. 2a-2c. For each output variable, three fuzzy sets, "Increase (I)", "No change (N)", and "Decrease (D)", are defined with membership functions $[g_i^I(x), g_i^N(x), g_i^D(x), i=TV, CO, NT]$. For the target volume, these three membership functions are shown in FIG. 2d.

Similar membership functions are defined for critical organ and normal tissues for the same adjustment strategy.

Based on the input and output variables defined above, fuzzy rules are established for the fuzzy inference engine. Eight rules are employed in the system. In each rule, the "if" part of rule is called antecedent and the "then" part of rule is called consequent. Two of them (Rule 5 and Rule 8) are used to demonstrate the procedure of fuzzy inference as shown in FIG. 3. Note that the input (output) variables are labeled using the bold fonts and their corresponding linguistic tags are labeled using the italic fonts in each rule. According to the linguistic tags, the corresponding membership functions for the input fuzzification are specified as shown in Step 1 of FIG. 3. Such as the input variable $C_{TV}$, the membership function $f_{TV}^H$ is specified in Rule 5 by the linguistic tag "High". For each rule, the outputs of the fuzzification are $[D^5_{TV}, D^5_{CO}, D^5_{NT}]$ and $[D^8_{TV}, D^8_{CO}, D^8_{NT}]$, respectively. Based on these outputs of fuzzification, the degree of support ($D_{SUPPORT}$) for each rule is achieved by a logic operator "Min", such as $D^5_{support}$=Min ($D^5_{TV}, D^5_{CO}, D^5_{NT}$) and $D^8_{support}$=Min ($D^8_{TV}, D^8_{CO}, D^8_{NT}$), as shown in Step 2 of FIG. 3. The degree of support represents the applicability of the rule's antecedent for given inputs. Based on the degree of supports, the fuzzy inference is performed by a standard implication method, which is accomplished by a logic operator "Min". For example in Step 3, the membership function $g^N_{TV}(x)$ in Rule 5 is modified as $g^{N,D5}_{TV}(x)$=Min ($D^5_{support}, g^N_{TV}(x)$). The modified membership functions became $[g^{N,D5}_{TV}(x), g^{N,D5}_{CO}(x), g^{N,D5}_{NT}(x)]$ and $[g^{N,D8}_{TV}(x), g^{N,D8}_{CO}(x), g^{N,D8}_{NT}(x)]$ for Rule 5 and Rule 8, respectively. As there are two sets of modified membership functions obtained, it is necessary to combine them to produce a single one. In Step 4, the functions were aggregated into one set by a logic operator "Max", i.e., $$[\overline{g_{TV}}(x), \overline{g_{CO}}(x), \overline{g_{NT}}(x)] = [\text{Max}(g_{TV}^{N,D5}(x), g_{TV}^{N,D8}(x)), \text{Max}(g_{CO}^{N,D5}(x), g_{CO}^{N,D8}(x)), \text{Max}(g_{NT}^{N,D5}(x), g_{NT}^{N,D8}(x))].$$

The aggregated functions represent the combined consequent from all the rules. Finally, the aggregated functions are defuzzified to a single value by the centroid method in Step 5. The x-coordinate of the centroid (represented by sign "⊕") for each aggregated function was the final output, the adjustment amount of weighting factors.

The Fuzzy Logic Guided Inverse Planning Algorithm

The flow chart of the FLGIP system is schematically illustrated in FIG. 4. First, the dose prescription and weighting factors are set to their initial values. Then, an iterative gradient algorithm is used to calculate the intensity spectrum x. In the study, the objective function is defined as follows:

$$f(x) = \sum_i \sum_j \sum_k w_{ijk}(p_{ijk} - d_{ijk})^2, \quad (1)$$

Where $$d_{ijk} = \sum_{n=1}^{N} A_{n,ijk} x_n$$

is the calculated dose for each voxel, $A_{n,ijk}$ is the relative dose coefficient, or dose per unit intensity of pencil beam. $P_{ijk}$ is the dose prescription and $w_{ijk}$ is the weighting factor defined as follows:

$$p_{ijk} = \begin{cases} P_{TV}, & \text{if } (i, j, k) \in \Omega_{TV} \\ P_{CO}, & \text{if } (i, j, k) \in \Omega_{CO} \\ P_{NT}, & \text{if } (i, j, k) \in \Omega_{NT} \end{cases}$$

$$w_{ijk} = \begin{cases} W_{TV}, & \text{if } (i, j, k) \in \Omega_{TV} \\ W_{CO}, & \text{if } (i, j, k) \in \Omega_{CO} \\ W_{NT}, & \text{if } (i, j, k) \in \Omega_{NT} \end{cases}$$

$\Omega w_{TV}$, $\Omega w_{CO}$ and $\Omega w_{NT}$ denote the target volume, the critical organ volume, and the normal tissue volume, respectively. The minimization of the objective function under the constraint of $x_n \geq 0$ can be written as a problem of $$\min_x \{f(x)\} \quad (2)$$

subject to $x_n \geq 0, \forall n$.

Equation 2 can be solved by the fast-monotonic-descent (FMD) method developed by Li and Yin, which is an optimized iterative gradient technique for the quadratic function. Based on the optimized intensity spectrum, the characteristic doses are calculated and then input to the FIS. Using fuzzy inference, the adjustment amounts of weighting factors [$\Delta W_{TV}$, $\Delta W_{CO}$, $\Delta W_{NT}$] are obtained. Then, the weighing factors for the next iteration are modified as follows:

$$W_i(n+1) = W_i(n)[1+\Delta W_j] i \in \{TV, CO, NT\}, \Delta W \in [-1,1]. \quad (3)$$

As the weighting factors affect the output of inverse planning by their relative values rather than the absolute values, they are re-normalized to [0, 1] by the following formula:

$$W_i^*(n+1) = \frac{W_i(n+1)}{\sqrt{W_{TV}(n+1)^2 + W_{CO}(n+1)^2 + W_{NT}(n+1)^2}} \quad (4)$$

$i \in \{TV, CO, NT\}$.

This updating procedure repeats until the following convergence criterion (5) is satisfied:

$$\frac{\sqrt{[C_{TV}(n+1) - C_{TV}(n)]^2 + [C_{CO}(n+1) - C_{CO}(n)]^2 + [C_{NT}(n+1) - C_{NT}(n)]^2}}{\sqrt{C_{TV}(n)^2 + C_{CO}(n)^2 + C_{NT}(n)^2}} < T. \quad (5)$$

where T is a small threshold number, such as 0.01.

Results

The performance of FLGIP system was examined using two cases (one simulated and one clinical). Dose-volume histograms (DVHs), plus the variation of characteristic doses and weighting factors versus the iteration number, are used as the primary tools to evaluate the performance of this system. Pencil beams of 6 MV were used. For simplicity, the primary-only dose at depth is used in the calculation. The initial weighting factors [$W_{TV}$, $W_{CO}$, $W_{NT}$] are set to [1,1,1] (after re-normalization using formula (4), they became [0.58, 0.58, 0.58]) and the convergence constant T was set to 0.01.

The Simulated Case

Figure 5A:
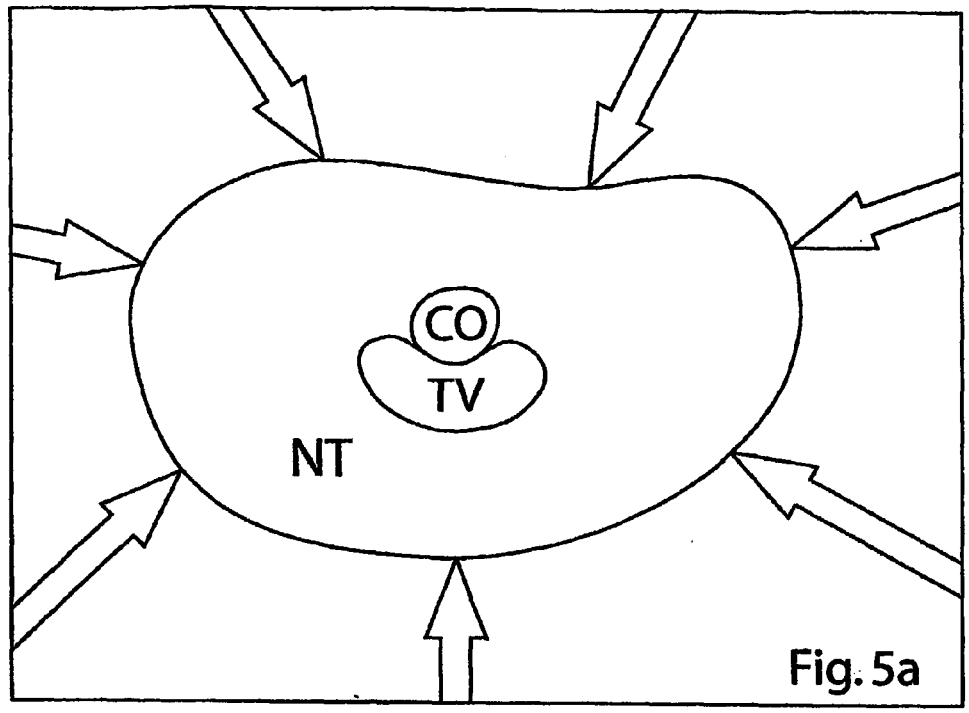
FIGS. 5A and B show the central slices for (FIG. 5A) a simulated case and (FIG. 5B) a clinical case, wherein TV, CO and NT represent the target volume, the critical organ and the normal tissue, respectively and arrows pointed to the target volume indicate the beam directions.

The central slice of this case is illustrated in FIG. 5a. The layout on this slice simulates the spinal cord with a target volume surrounding it. Seven treatment beams are uniformly arranged between 360 degrees. The configuration is typical in spinal radiosurgery using IMRT.

The FLGIP system was tested using four sets of different dose prescriptions: [100%, 20%, 50%], [100%, 30%, 50%], [100%, 40%, 50%], [100%, 50%, 50%]. FIG. 6 shows the variation of (a) characteristic doses and (b) weighting factors versus the iteration number for dose prescription [100%, 30%, 50%]. The results indicate that for the target volume and critical organ, the characteristic doses monotonically converge to the prescribed doses (the normal tissue dose also converges, but at a much less rate due to its large volume.) The results shown in Table 1 demonstrate that the high target dose and low critical organ dose are achieved simultaneously and both meet the prescribed doses. The corresponding DVHs for (a) the target volume, (b) the critical organ, and (c) the normal tissue are shown in FIG. 7. The final results also depend on the provided dose prescriptions. For each set of dose prescriptions, the corresponding isodose distributions are shown in FIG. 8.

The effect of initial weighting factors on the final characteristic doses was examined by using eight sets of initial values with the same dose prescriptions [100%, 30%, 50%]. The characteristic doses for each set converged within 50 iterations. The final results and the standard deviations are shown in Table 2. The results indicate that the achieved characteristic doses by different sets of initial weighting factors are comparable. The final eight sets of weighting factors were averaged. The mean weighting factors and their standard deviations are 0.139±0.113 for the target volume, 0.985±0.025 for the critical organ, and 0.004±0.003 for the normal tissue.

The Clinical Case

Figure 5B:
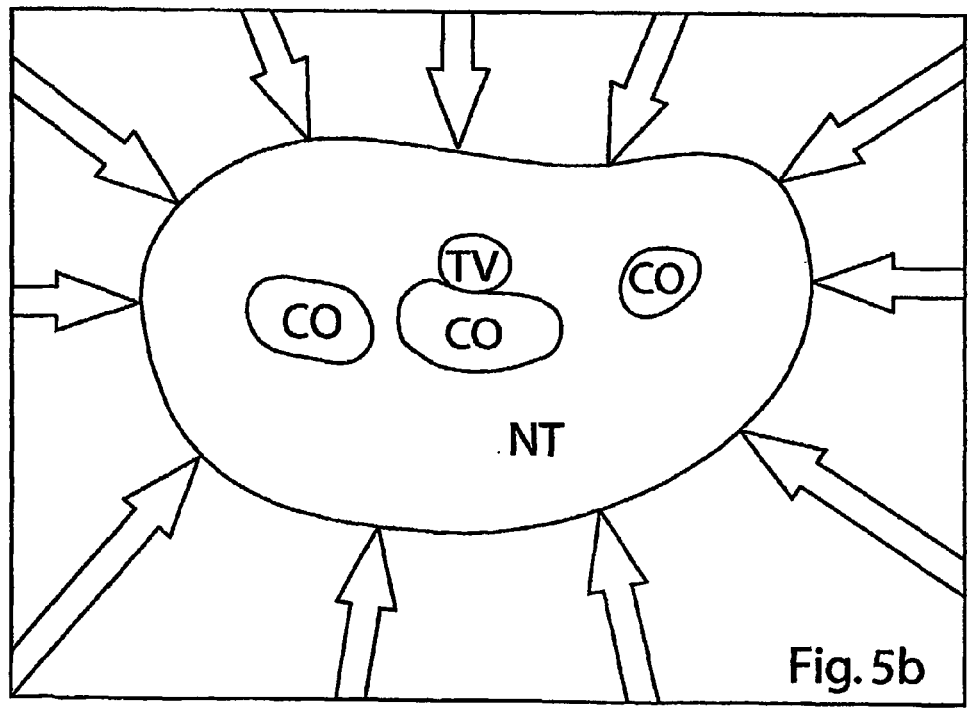
Figure 11:
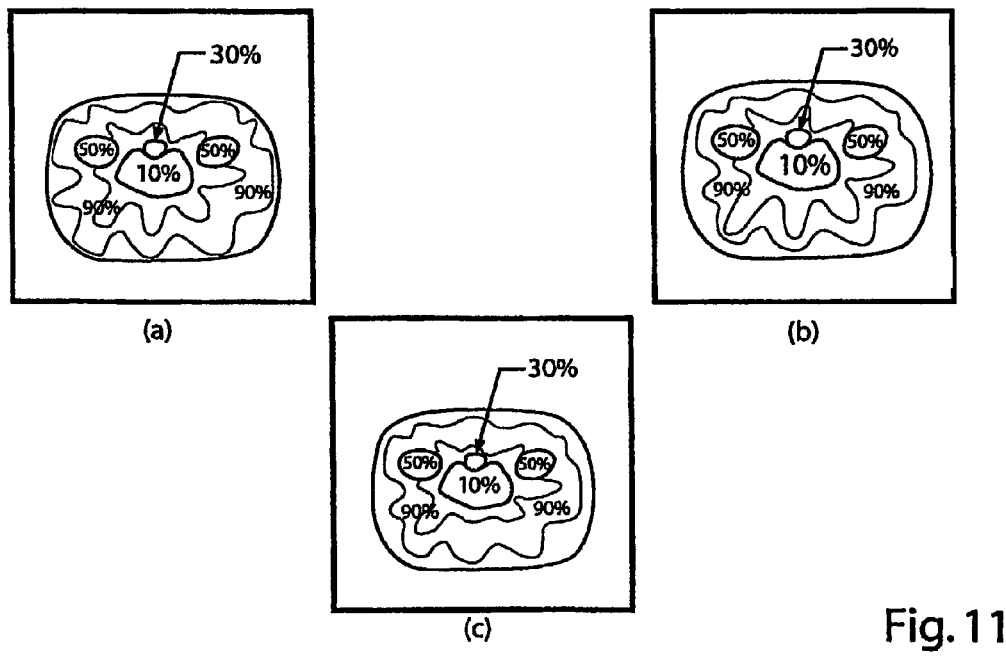
FIGS. 11A-C show the dose distributions in the clinical case at (FIG. 11A) Iteration 5, (FIG. 11B) Iteration 10, and (FIG. 11C) Iteration 15.

The central slice for the present study is illustrated in FIG. 5b. Eleven beams are arranged at 0°, 33°, 66°, 90°, 120°, 150°, 210°, 240°, 270°, 300°, 330°. The configuration represents a complicated IMRT case. The dose prescription is set to [100%, 30%, 50%]. The variations of the characteristic doses and weighting factors versus the iteration number are shown in FIG. 9a and FIG. 9b, respectively. The characteristic dose $C_{TV}$ monotonically converges to its prescribed dose 100% while the characteristic doses $C_{CO}$ and $C_{NT}$ monotonically converges to the doses below their prescribed values, 30% and 50% respectively. The DVHs of the calculated doses for different organs at three iterations 5, 10, 15 are shown in FIG. 10. The results indicate that the gap between the DVHs of target volume (FIG. 10a) and critical organs (FIG. 10c) increases with increased iteration number. The substantial improvements of isodose distributions around the critical organ $CO_1$, (the one closet to target volume) in different iterations can be easily identified from FIG. 11.

Discussion

A fuzzy inference system was developed to automatically modify the weighting factors in inverse treatment planning in order to achieve the dose distributions best matching the treatment requirements. The fundamental inference mechanism is demonstrated by a mini system consisted of rules as shown in FIG. 3. Among the eight rules, Rule 5 plays the primary role to drive the system toward the convergence while Rule 8 (plus the other six rules) drives the inputs toward its prescribed ones. For example, when the inputs for critical organ and normal tissue are much higher than their prescribed doses, the output of FIS can mainly be determined by the adjustment of Rule 8. Once the inputs approach their prescribed ones to better match the antecedent of Rule 5 (usually after several iterations), the consequent of Rule 5 takes more effect on the output of FIS and drives the system towards convergence. The other six rules are used to process different scenarios of mismatching between characteristic doses and prescribed doses of different organs.

The details of the adjustment process are shown in FIG. 6 and FIG. 9. At the first several iterations, the weighting factor for the target volume decreases and the weighting factor for the critical organs increases quickly. After a few iterations, as the characteristic doses approach the prescribed ones, the adjustments of weighting factors gradually reduce. The characteristic doses for the target and critical organs in the last iteration satisfy their dose prescriptions. For the normal tissue, however, the final characteristic dose is appreciably lower than its prescribed dose due to its large volume. Although some rules seemingly take less effect on or are seldom used in these two cases, these rules are necessary for the more complicated cases. In addition, the results shown in FIG. 7 indicate that using different dose prescriptions can result in different dose distributions. Potentially, the fuzzy inference technique can also be used to optimize other parameters in inverse planning such as the beam orientation, the dose prescription, etc.

As the configuration of FIS is flexible, it provides a wide space to customize the configuration for different applications. In the system, the input characteristic doses are chosen as the mean dose combined with its standard deviation. For target, the lower than mean input dose helps the FIS to drive the target dose to be higher toward the prescribed one in the next iteration. Similarly, for critical organ and normal tissue, the higher than mean input dose drives critical and normal tissue doses to be lower toward the prescribed ones in the next iteration. In this way, both high target dose and lower critical organ (and normal tissue) doses can be easier to achieve. For output variables, they are simply defined as the relative adjustment of the weighting factors, which are between −1 and 1. For the selection of inference rules, it is primarily determined by the clinical experience. The general treatment intention can be described as: If the target dose is low, its weighting factor should be increased. If the critical organ and normal tissue doses are high, their weighting factors should be increased. In the system of the present invention, such treatment intention is expressed by eight rules, which is a complete combination of linguistic tags for three kinds of involved organs. The option can avoid any unpredicted input values. As for the selection of membership functions, the Gaussian function is adopted due to its simplicity and popularity for most of the engineering applications. In some circumstances, part of the Gaussian function is used, such as those shown in FIG. 2a-2c.

CONCLUSION

A fuzzy logic guided inverse planning system has been developed. The system provides an effective and efficient approach to optimize the parameters used in inverse planning. The main advantage of using FIS is that it can perform the sophisticated inference formerly done by trial-and-error approach. Relying on the planner's experience and knowledge on how to compromise parameters among different organs involved, the optimization of weighting factors can be easily accomplished by encoded rules. As demonstrated by the result of two cases, the fuzzy inference system can undertake the very complex task of parameter optimization in inverse planning.

Throughout the application, author and year and patents by number reference various publications, including United States patents. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

TABLE I

Comparison of results by using different sets of dose prescriptions.

| Dose prescription (%) | | | Calculated dose (%) | | | | | |
|---|---|---|---|---|---|---|---|---|
| | | | Target volume | | Critical organ | | Normal tissue | |
| Target volume | Critical organ | Normal tissue | Mean | STD | Mean | STD | Mean | STD |
| 100 | 20 | 50 | 102.1 | 6.3 | 20.5 | 2.4 | 26.2 | 18.9 |
| 100 | 30 | 50 | 102.3 | 5.3 | 31.1 | 2.1 | 26.6 | 19.1 |
| 100 | 40 | 50 | 102.3 | 4.6 | 40.2 | 1.8 | 26.9 | 18.7 |
| 100 | 50 | 50 | 102.4 | 4.1 | 50.3 | 2.0 | 27.2 | 18.6 |

TABLE II

Comparison of results by using different sets of initial weighting factors.

| Weighting factor | | | Calculated dose (%) | | | | | |
|---|---|---|---|---|---|---|---|---|
| | | | Target volume | | Critical organ | | Normal tissue | |
| Target volume | Critical organ | Normal tissue | Mean | STD | Mean | STD | Mean | STD |
| 0.1 | 0.1 | 0.1 | 100.8 | 5.6 | 30.2 | 0.8 | 25.8 | 18.8 |
| 0.1 | 0.1 | 1.0 | 101.0 | 5.9 | 30.0 | 0.2 | 25.7 | 19.1 |
| 0.1 | 1.0 | 0.1 | 101.1 | 6.0 | 30.0 | 0.2 | 25.7 | 19.1 |
| 1.0 | 0.1 | 0.1 | 100.3 | 4.5 | 30.8 | 3.0 | 25.3 | 18.5 |
| 1.0 | 1.0 | 1.0 | 100.8 | 5.6 | 30.2 | 0.8 | 25.8 | 18.8 |
| 1.0 | 1.0 | 0.1 | 100.5 | 5.1 | 30.4 | 1.5 | 25.5 | 18.6 |
| 1.0 | 0.1 | 1.0 | 100.4 | 5.2 | 30.3 | 1.3 | 25.3 | 18.7 |
| 0.1 | 1.0 | 1.0 | 100.7 | 6.0 | 30.0 | 0.1 | 26.6 | 22.5 |

What is claimed is:

1. A fuzzy inference system for use in modulating radiation treatment, said system comprising:
    single input fuzzifier means for inputting and optimizing singular imaging data and a physician's treatment intention including dose/volume constraints for critical organs, normal tissues, targets and compromising strategy between critical organs, normal tissues, and targets;
    inference means operatively connected to said fuzzifier means, said inference means for analyzing the imaging data and the physician's treatment intention and determining radiation treatment target from non-treatment target; and defuzzifier means for modulating radiation treatment pursuant to the analysis from said inference means.

2. The system according to claim 1, wherein said system is computer based.

3. A method of modulating radiation treatment by:
inputting patient data into the fuzzy inference system according to claim 1;
and modulating radiation treatment pursuant to data obtained from the fuzzy inference system.

4. The method according to claim 3, wherein said modulating step includes automatically modulating radiation treatment.

5. The method according to claim 4, wherein said modulating step includes automatically modulating radiation treatment via a computer.

6. The method according to claim 3, wherein said modulating step includes increasing the amount of radiation at a specified location.

7. The method according to claim 3, wherein said modulating step includes decreasing the amount of radiation at a specified location.

8. An apparatus for producing modulating radiation therapy in patients, said apparatus comprising:

an imaging device for creating and storing image data of relevant tissue and organ parts; and
a fuzzy inference system according to claim 1, said system operatively connected to said imaging device for modulating radiation treatment.

9. The apparatus according to claim 8, wherein said system is computer based.

10. A fuzzy inference system for use in modulating radiation treatment, said system comprising:
single input fuzzifier means for inputting and optimizing singular imaging data and a physician's treatment intention including dose/volume constraints for critical organs, normal tissues, targets and compromising strategy between critical organs, normal tissues, and targets;
inference means operatively connected to said fuzzifier means, said inference means for analyzing the imaging data and the physician's treatment intention and determining strength of radiation treatment; and
defuzzifier means for modulating radiation treatment pursuant to the analysis from said inference means.

11. The system according to claim 10, wherein said system is computer based.

* * * * *